(12) United States Patent
Chan et al.

(10) Patent No.: US 9,402,754 B2
(45) Date of Patent: Aug. 2, 2016

(54) EXPANDABLE ENDOPROSTHESES, SYSTEMS, AND METHODS FOR TREATING A BIFURCATED LUMEN

(75) Inventors: Gregory W. Chan, San Francisco, CA (US); John F. Boylan, Murrieta, CA (US); Carol M. Lee, Santa Clara, CA (US); Laura M. Kalvass, Mountain View, CA (US); Barbara E. Stamberg, San Jose, CA (US)

(73) Assignee: ABBOTT CARDIOVASCULAR SYSTEMS, INC., Santa Clara, CA (US)

(*) Notice: Subject to any disclaimer, the term of this patent is extended or adjusted under 35 U.S.C. 154(b) by 890 days.

(21) Appl. No.: 12/782,399

(22) Filed: May 18, 2010

(65) Prior Publication Data

US 2011/0288622 A1  Nov. 24, 2011

(51) Int. Cl.
*A61F 2/06* (2013.01)
*A61F 2/915* (2013.01)
*A61F 2/954* (2013.01)

(52) U.S. Cl.
CPC .............. *A61F 2/915* (2013.01); *A61F 2/954* (2013.01); *A61F 2002/065* (2013.01); *A61F 2002/91525* (2013.01); *A61F 2002/91558* (2013.01); *A61F 2002/91575* (2013.01); *A61F 2210/0076* (2013.01); *A61F 2230/0054* (2013.01)

(58) Field of Classification Search
CPC .............. A61F 2/91; A61F 2230/0054; A61F 2210/0076; A61F 2/954; A61F 2002/91525; A61F 2002/91575; A61F 2002/065; A61F 2002/91558; A61F 2/88; A61F 2/89; A61F 2/90

USPC ................ 623/1.11, 1.15, 1.35; 606/108
See application file for complete search history.

(56) References Cited

U.S. PATENT DOCUMENTS

| | | | |
|---|---|---|---|
| 4,877,031 | A | 10/1989 | Conway et al. |
| 4,909,258 | A | 3/1990 | Kuntz et al. |
| 4,994,071 | A | 2/1991 | MacGregor |
| 5,156,619 | A | 10/1992 | Ehrenfeld |
| 5,458,585 | A | 10/1995 | Salmon et al. |
| 5,496,365 | A | 3/1996 | Sgro |
| 5,507,767 | A | 4/1996 | Maeda et al. |
| 5,571,073 | A | 11/1996 | Castillo |
| 5,643,340 | A | 7/1997 | Nunokawa |
| 5,741,429 | A | 4/1998 | Donadio, III et al. |
| 5,795,331 | A | 8/1998 | Cragg et al. |

(Continued)

FOREIGN PATENT DOCUMENTS

| | | |
|---|---|---|
| EP | 0 492 361 | 7/1996 |
| EP | 0 891 751 | 1/1999 |

(Continued)

OTHER PUBLICATIONS

U.S. Appl. No. 11/683,995, Jul. 20, 2011, Office Action.

(Continued)

*Primary Examiner* — Richard Louis
(74) *Attorney, Agent, or Firm* — Workman Nydegger; John Kwok

(57) ABSTRACT

An endoprosthesis for treating a bifurcated lumen. The distal end of the endoprosthesis can include at least two wings and at least two troughs so the endoprosthesis can adequately scaffold the ostium of a bifurcated lumen by at least partially straddling the carina of the lumen bifurcation. The distal end of the endoprosthesis can also be configured to have increased expandability to help allow conformity to the anatomy of a bifurcated lumen.

27 Claims, 22 Drawing Sheets

(56) References Cited

U.S. PATENT DOCUMENTS

| | | | |
|---|---|---|---|
| 5,800,520 A | 9/1998 | Fogarty et al. | |
| 5,824,036 A * | 10/1998 | Lauterjung | 623/1.11 |
| 5,827,320 A | 10/1998 | Richter et al. | |
| 5,830,155 A | 11/1998 | Frechette et al. | |
| 5,860,963 A | 1/1999 | Azam et al. | |
| 5,906,640 A | 5/1999 | Penn et al. | |
| 5,938,697 A * | 8/1999 | Killion et al. | 623/1.15 |
| 6,001,124 A | 12/1999 | Bachinski | |
| 6,096,073 A | 8/2000 | Webster et al. | |
| 6,165,195 A | 12/2000 | Wilson et al. | |
| 6,179,878 B1 | 1/2001 | Duerig et al. | |
| 6,183,509 B1 * | 2/2001 | Dibie | 623/1.35 |
| 6,210,431 B1 | 4/2001 | Power | |
| 6,258,116 B1 * | 7/2001 | Hojeibane | 623/1.16 |
| 6,264,686 B1 | 7/2001 | Rieu et al. | |
| 6,346,089 B1 | 2/2002 | Dibie | |
| 6,436,104 B2 | 8/2002 | Hojeibane | |
| 6,475,209 B1 | 11/2002 | Larson et al. | |
| 6,488,702 B1 * | 12/2002 | Besselink | 623/1.15 |
| 6,491,719 B1 | 12/2002 | Fogarty et al. | |
| 6,494,905 B1 | 12/2002 | Zedler et al. | |
| 6,500,147 B2 | 12/2002 | Omaleki et al. | |
| 6,527,790 B2 | 3/2003 | Chien et al. | |
| 6,530,897 B2 | 3/2003 | Nardeo | |
| 6,562,067 B2 * | 5/2003 | Mathis | 623/1.16 |
| 6,579,309 B1 | 6/2003 | Loos et al. | |
| 6,585,758 B1 * | 7/2003 | Chouinard et al. | 623/1.16 |
| 6,666,884 B1 | 12/2003 | Webster | |
| 6,676,691 B1 | 1/2004 | Hosny | |
| 6,692,483 B2 | 2/2004 | Vardi et al. | |
| 6,730,103 B2 | 5/2004 | Dakov | |
| 6,855,123 B2 | 2/2005 | Nita | |
| 6,964,681 B2 * | 11/2005 | Murray, III | 623/1.15 |
| 7,105,012 B2 | 9/2006 | Trout, III | |
| 7,105,020 B2 | 9/2006 | Greenberg et al. | |
| 7,169,176 B2 | 1/2007 | Lauterjung | |
| 7,252,679 B2 * | 8/2007 | Fischell et al. | 623/1.11 |
| 7,323,009 B2 | 1/2008 | Suhr et al. | |
| 7,344,557 B2 | 3/2008 | Yadin | |
| 7,578,831 B2 | 8/2009 | Von Oepen et al. | |
| 2001/0027291 A1 | 10/2001 | Shanley | |
| 2002/0077651 A1 | 6/2002 | Holmes, Jr. et al. | |
| 2002/0111665 A1 | 8/2002 | Lauterjung | |
| 2003/0187494 A1 | 10/2003 | Loaldi | |
| 2004/0158143 A1 | 8/2004 | Flaherty et al. | |
| 2004/0193254 A1 | 9/2004 | Greenberg et al. | |
| 2004/0225345 A1 | 11/2004 | Fischell et al. | |
| 2004/0236405 A1 * | 11/2004 | Kula et al. | 623/1.15 |
| 2005/0038500 A1 * | 2/2005 | Boylan et al. | 623/1.18 |
| 2005/0060027 A1 | 3/2005 | Khenansho et al. | |
| 2005/0084130 A1 | 4/2005 | Yamagishi | |
| 2005/0119606 A1 | 6/2005 | Nita | |
| 2005/0177221 A1 * | 8/2005 | Mustapha | 623/1.11 |
| 2005/0261757 A1 * | 11/2005 | Shanley | A61F 2/915 |
| | | | 623/1.15 |
| 2005/0288771 A1 * | 12/2005 | Majercak et al. | 623/1.15 |
| 2006/0025843 A1 | 2/2006 | Gurm et al. | |
| 2006/0079956 A1 | 4/2006 | Eigler et al. | |
| 2006/0100694 A1 | 5/2006 | Globerman | |
| 2006/0155360 A1 * | 7/2006 | Calisse et al. | 623/1.15 |
| 2006/0282154 A1 | 12/2006 | Oepen et al. | |
| 2007/0088428 A1 | 4/2007 | Teichman | |
| 2007/0150048 A1 * | 6/2007 | Tischler | A61F 2/88 |
| | | | 623/1.16 |
| 2007/0260217 A1 | 11/2007 | Von Oepen | |
| 2007/0260224 A1 | 11/2007 | Von Oepen | |
| 2007/0270933 A1 * | 11/2007 | Von Oepen et al. | 623/1.11 |
| 2008/0046066 A1 | 2/2008 | Jenson et al. | |
| 2008/0046072 A1 * | 2/2008 | Laborde et al. | 623/1.34 |
| 2009/0259286 A1 * | 10/2009 | Ohri | A61F 2/958 |
| | | | 623/1.11 |
| 2009/0287299 A1 * | 11/2009 | Tabor et al. | 623/1.26 |
| 2012/0209368 A1 | 8/2012 | Oepen et al. | |

FOREIGN PATENT DOCUMENTS

| | | |
|---|---|---|
| EP | 1 293 178 | 3/2003 |
| EP | 1 512 380 | 8/2007 |
| WO | WO 97/07752 | 3/1997 |
| WO | WO 98/36709 | 8/1998 |
| WO | WO 02/13727 | 2/2002 |
| WO | WO 02/47591 | 6/2002 |
| WO | WO 03/088871 | 10/2003 |
| WO | WO 2005/084130 | 9/2005 |
| WO | WO 2007/104051 | 9/2007 |
| WO | WO 2007/104056 | 9/2007 |
| WO | WO 2007/130739 | 11/2007 |

OTHER PUBLICATIONS

U.S. Appl. No. 11/683,999, Aug. 17, 2011, Office Action.
U.S. Appl. No. 11/683,995, Dec. 28, 2011, Notice of Allowance.
U.S. Appl. No. 11/683,999, Jan. 26, 2012, Office Action.
U.S. Appl. No. 11/683,995, Feb. 8, 2012, Notice of Allowance.
U.S. Appl. No. 11/683,999, Feb. 8, 2012, Office Action.
U.S. Appl. No. 60/780,752, filed Mar. 9, 2006, Von Oepen.
U.S. Appl. No. 11/683,995, Feb. 19, 2010, Office Action.
U.S. Appl. No. 11/683,995, Jun. 24, 2010, Office Action.
U.S. Appl. No. 11/683,995, Jan. 20, 2011, Office Action.
U.S. Appl. No. 11/683,997, Apr. 27, 2010, Office Action.
U.S. Appl. No. 11/683,997, Jul. 9, 2010, Office Action.
U.S. Appl. No. 11/683,997, Nov. 23, 2010, Office Action.
U.S. Appl. No. 11/683,999, Feb. 19, 2010, Office Action.
U.S. Appl. No. 11/683,999, Apr. 28, 2010, Office Action.
U.S. Appl. No. 11/683,999, Oct. 27, 2010, Office Action.
U.S. Appl. No. 11/683,995, Apr. 5, 2012, Notice of Allowance.
U.S. Appl. No. 13/458,768, Dec. 24, 2012, Office Action.
U.S. Appl. No. 13/458,768, May 29, 2013, Office Action.

* cited by examiner

EXPANDABLE ENDOPROSTHESES, SYSTEMS, AND METHODS FOR TREATING A BIFURCATED LUMEN

CROSS-REFERENCE TO RELATED APPLICATIONS

Not applicable.

BACKGROUND OF THE INVENTION

1. Technology Field

The present invention generally relates to implantable medical devices and delivery systems for implantable medical devices used in intravascular systems. In particular, the present invention relates to implantable medical device that are shaped and configured for placement within a bifurcated lumen of a human or animal.

2. The Related Technology

Stents, grafts, and a variety of other implantable medical devices or prostheses used in interventional procedures, such as for treating aneurysms, for lining or repairing vessel walls, for filtering or controlling fluid flow, and for expanding or scaffolding occluded or collapsed vessels. Such implantable medical devices can be delivered and used in virtually any accessible body lumen of a human or animal, and can be deployed by any of a variety of recognized means. One recognized use of an implantable medical device, such as a stent, is the treatment of atherosclerotic stenosis in blood vessels. For example, after a patient undergoes a percutaneous transluminal coronary angioplasty or similar interventional procedure a stent is often deployed at the treatment site to improve the results of the medical procedure and reduce the likelihood of restenosis. The stent is configured to scaffold or support the treated blood vessel; if desired, it can also be loaded with a beneficial agent so as to act as a delivery platform to reduce restenosis or the like.

Conventional implantable medical devices are typically designed to treat or repair lumens of a vessel or other tubular organ that are removed from bifurcations. It is often necessary, however, to repair or treat the lumen of a vessel or other tubular organ at or near a point of bifurcation. Using conventional implantable medical devices to treat lumen bifurcations presents various drawbacks and can be challenging. For example, due to the generally, straight tubular design of conventional implantable medical devices, several implantable medical devices are typically required to completely cover a bifurcated lumen. The use of multiple implantable medical devices can significantly increase the complexity of implanting the implantable medical devices, can result in the overlapping of implantable medical devices, and can nonetheless lead to inadequate scaffolding due to gaps between endoprostheses.

The use of a single conventional implantable medical device to treat a bifurcated lumen can also present various difficulties. For example, it is common to implant the proximal end of a conventional endoprosthesis within the main lumen of a bifurcated lumen and extend the distal end of the endoprosthesis into one of the lumen side branches. This type of placement may compromise the patency of the bifurcation by jailing off the other lumen side branch. So called "endoprosthesis jails" can restrict blood flow into, and prevent future treatment of, the distal portion of the jailed lumen branch.

Furthermore, when the bifurcated lumen is an artery or other vessel being treated due to atheroma, plaque can easily be shifted from the treated main lumen to the non-treated lumen branches, thereby occluding one or both of the lumen side branches. This is known as the "snowplow" effect. In addition to occluding one or both of the lumen branches, a dislodged atheroma can be swept downstream into one of the lumen side branches, which can pose high threats to patient safety. Other complications that may arise when using conventional endoprostheses to treat bifurcated lumens include vessel spasm, thrombosis, and embolism.

One reason conventional endoprostheses are typically inadequate for treating bifurcated lumens is that they do not account for the variation in lumen size that can occur at or near the bifurcation of a lumen. For instance, it is common for the diameter of the main lumen to increase near the ostium of the lumen side branches. Furthermore, depending upon the location of the bifurcated lumen, the size of the main lumen may vary along its length.

For example, at the left main region of a patient's anatomy, the left main vessel extends from the aorta and bifurcates into the left circumflex vessel and the crucial left anterior descending vessel. Due to the proximity of the left main vessel to the aorta, the size of the left main vessel can be quite large and vary along its length. The inability of conventional endoprostheses to compensate for variation in vessel size often means that the endoprostheses are either oversized or undersized, both of which can lead to severe complications. In particular, an endoprosthesis that is undersized may cause thrombus formation, whereas an endoprosthesis that is oversized may result in vessel rupture.

Additionally, conventional endoprostheses typically do not account for varying lesion characteristics that may be particular to a bifurcated is common for a lesion to build along lateral edges of the ostium in a circumferential manner, but not to form on the carina of the bifurcation (as used herein the term "carina" refers to the apex of a lumen bifurcation where the side branches split off from the main lumen). When treating such a lesion with conventional endoprostheses, the carina is often nonetheless contacted and supported by the endoprosthesis. In such cases, however, it may not be necessary or desirable to contact the carina. For example, contacting the carina can cause restenosis at the carina or otherwise damage the carina.

BRIEF SUMMARY OF THE INVENTION

Briefly summarized, implementations of the present invention provide systems, methods, and apparatus for treating bifurcated lumens that account for anatomy and lesion characteristics common at lumen bifurcations. For example, one or more implementations of the present invention include an expandable implantable medical device or prosthesis having a distal end configured to allow the device to conform to the anatomy of a bifurcated lumen. In particular, the distal end of the implantable endoprosthesis can include at least two wings and at least two troughs that provide the distal end with increased expandability. The endoprosthesis of the present invention can provide optimal scaffolding of a bifurcated lumen by covering the main lumen proximate the bifurcation and the lateral sides of the lumen side branches.

For example, in one configuration, an expandable endoprosthesis a tubular body having a distal end and a proximal end. The distal end of the tubular body can include distally extending wing portions and proximally extending recesses. The distally extending wing portions and the proximally extending recessed can be formed from concentric rings having alternating crests and valleys aligned in a wave pattern.

In another configuration, an expandable endoprosthesis can include a tubular body having a distal end and a proximal end. The proximal end of the body can be configured to expand from a contracted diameter to a first expanded diameter. At least a portion of the distal end of the body can be configured to expand from the contracted diameter to a second expanded diameter that is larger than the first expanded diameter. Additionally, the distal end can include distally extending wing portions formed from a web structure having a plurality of alternating crests and valleys.

In another configuration, an expandable, intraluminal endoprosthesis can include a tubular body having proximal and distal ends with a lumen extending therebetween. The endoprosthesis can also include wing portions extending distally from the distal end of the tubular body. The wing portions can include a web structure having alternating crests and valleys. Additionally, the endoprosthesis can have recessed portions that extend proximately into the distal end of the tubular body. The distal end of the endoprosthesis can be configured in size and shape such that when deployed proximate a bifurcated lumen, the recessed portions can straddle the carina of the bifurcated lumen, and the wing portions can extend into and along the lateral walls of the side branches of the bifurcated lumen.

In yet another configuration, an expandable endoprosthesis for treating a bifurcated lumen can include a first set of concentric rings including a plurality of alternating crests and valleys defining a proximal end of a tubular body. At least one crest or valley of each concentric ring of the first set of concentric rings can be directly joined to a crest or valley of an adjacent concentric ring of the first set of concentric rings. The endoprosthesis can also include a second set of concentric rings including a plurality of alternating crests and valleys defining a distal end of the tubular body. At least one crest or valley of each concentric ring of the second set of concentric rings can be indirectly joined to a crest or valley of an adjacent concentric ring of the second set of concentric rings by one or more inter-connector elements. Additionally, the distal end of the tubular body can include at least two distally extending wing portions formed by the plurality of alternating crests and valleys of the second set of concentric rings.

In addition to the foregoing, an endoprosthesis deployment system can include a first guidewire for placement in a first side branch of a bifurcated lumen and a second guidewire for placement within a second side branch of the bifurcated lumen. The endoprosthesis deployment system can also include a delivery device for tracking along the first and second guidewires to a position proximate the carina of the bifurcated lumen. Additionally, the endoprosthesis deployment system can include an endoprosthesis having a tubular body having a distal end and a proximal end. The distal end can includes at least two distally extending wing portions formed from at least one concentric ring having a plurality of alternating crests and valleys aligned in a wave pattern.

Additionally, a method for delivering an endoprosthesis to a bifurcated lumen can include positioning a first guidewire within a main lumen of a patient proximate a lumen bifurcation such that it extends from the main lumen into a first lumen side branch. The method can also include positioning a second guidewire within the main lumen proximate the lumen bifurcation such that it extends from the main lumen into a second lumen side branch. The method can further include tracking a catheter including an endoprosthesis with a distal end having increased expandability along the first and second guidewires to a deployment position proximate the lumen bifurcation. The method can additionally include deploying the endoprosthesis such that the distal end covers the ostium of the lumen bifurcation without contacting carina of the lumen bifurcation.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. Furthermore, it should be noted that the figures are not drawn to scale and that elements of similar structures or functions are generally represented by like reference numerals for illustrative purposes throughout the figures. The invention will be described and explained with additional specificity and detail through the use of the accompanying drawings in which.

DETAILED DESCRIPTION OF THE PREFERRED EMBODIMENTS

Figure 1:
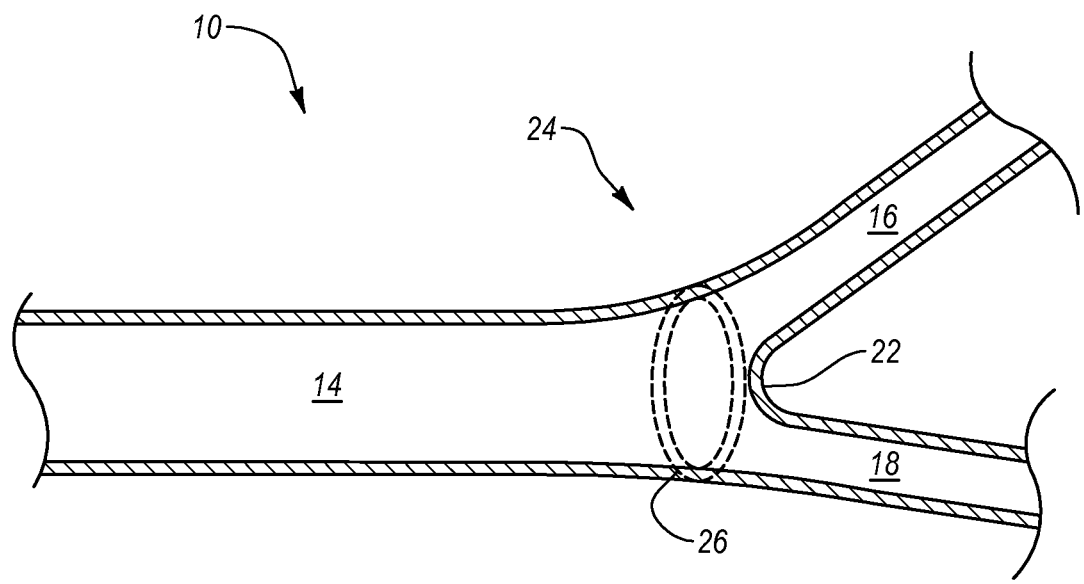
FIG. 1 illustrates a schematic of an exemplary bifurcated lumen in which implementations of the present invention can be practiced.

Implementations of the present invention include systems, methods, and apparatus for treating bifurcated lumens that account for anatomy and lesion characteristics common at lumen bifurcations. For example, one or more implementations of the present invention include an expandable implantable medical device or prosthesis having a distal end configured to allow the device to conform to the anatomy of a bifurcated lumen. In particular, the distal end of the implantable endoprosthesis can include at least two wings and at least two troughs that provide the distal end with increased expandability. The endoprosthesis of the present invention can provide optimal scaffolding of a bifurcated lumen by covering the main lumen proximate the bifurcation and the lateral sides of the lumen side branches.

Additionally, the systems, methods, and apparatus of the present invention can provide optimal scaffolding of a bifurcated lumen, while also preventing the traumatization of the carina. In particular, according to some implementations of the present invention the distal end of the endoprosthesis can include at least two troughs configured to be deployed around the carina and at least two wings configured to be deployed into and along the lateral sides of the lumen side branches. Also, at least the distal end of the endoprosthesis can include angled crests to help allow the endoprosthesis to extend into the side branches of a bifurcated lumen, while helping to ensure that the carina is only lightly contacted, if at all. Furthermore, the number of crests included in the distal end of the endoprosthesis can be configured to aid the endoprosthesis in conforming to the anatomy of a lumen bifurcation. For example, according to some implementations of the present invention, the distal end of the endoprosthesis can include ten crests.

Additionally, the distal end of the endoprosthesis of the present invention can have increased expandability to allow the device to conform to the anatomy of a bifurcated lumen. For example, according to some implementations of the present invention the distal end of the endoprosthesis can include arm bars to help ensure optimal expansion and flexibility by decoupling it from the proximal end of the endoprosthesis. Additionally, one or more implementations of the present invention can include an endoprosthesis with a distal end formed with walnut-shaped cells, which provide increased expansion and flexibility. One will appreciate in light of the disclosure herein that the increased expandability and flexibility of the distal end of the endoprosthesis can help ensure adequate scaffolding of the ostium of the bifurcation and other areas of body lumen with an increasing diameter. The increased expandability of the distal end of the endoprosthesis of the present invention can also help ensure that at least the lateral sides of the lumen side branches have adequate scaffolding.

Additional implementations of the present invention include an endoprosthesis with patterns or configurations that vary along the length of the endoprosthesis to allow the endoprosthesis to conform to and adequately scaffold the varying anatomy of a bifurcated lumen. For example, the proximal portion of the endoprosthesis can have a pattern that provides uniform expansion and radial strength. A central portion of the endoprosthesis can have a pattern that combines radial strength with improved flexibility. Finally, a distal portion of the endoprosthesis can include a pattern that helps increase expansion and flexibility. The different regions of the endoprosthesis can help the endoprosthesis to conform to the anatomy of the lumen bifurcation, help ensure that the endoprosthesis does not injure the carina, and help ensure that the endoprosthesis adequately scaffolds the lumen side branches.

Reference will now be made to Figures wherein like structures will be provided with like reference designations. One will understood that the drawings are diagrammatic and schematic representations of exemplary embodiments of the invention, and are not limiting of the present invention nor are they necessarily drawn to scale.

FIGS. 1-12B depict various features or aspects of implementations of the present invention, which is generally directed to an endoprosthesis configured to adequately scaffold a bifurcated lumen without causing trauma to the carina. The implantable medical devices or endoprostheses depicted in the Figures are stents, but it will be understood that the benefits and features of the present invention are also applicable to other types of endoprostheses or other medical devices. Thus, one will appreciate in light of the disclosure herein that such implantable medical devices or endoprostheses can include stents, filters, grafts, valves, occlusive devices, trocars, aneury treatment devices, or the like.

Reference is made to FIG. 1 in describing an exemplary environment in which implementations of the present invention can be practiced. FIG. 1 depicts a body lumen 10, including a bifurcation 24 where a main lumen 14 splits into first and second lumen side branches 16, 18 at an oblique intersection or carina 22. One will appreciate that the particular size and shape of the main lumen 14, lumen side branches 16, 18, bifurcation 24, ostium 26 of the bifurcation 24, and carina 22 are dependent on the particular type, structure, and location of body lumen 10. As such, the main lumen 14 and respective lumen side branches 16, 18 depicted in Figures are merely exemplary of the broader range of lumen configurations that can benefit from the present invention. For example, the exemplary environment depicted in FIG. 1 may be a coronary artery; however, one will appreciated in light of the disclosure herein that the endoprosthesis of the present invention can be configured for treatment of and deployment within a variety of intralumenal applications, including vascular, coronary, biliary, esophageal, urological, gastrointestinal, or the like.

In contrast to conventional endoprostheses, endoprostheses of the present invention are configured to be deployed to adequately cover most if not all of the ostium of a lumen bifurcation 24, including the lateral walls of the lumen side branches 16, 18. Endoprostheses of the present invention can provide optimal scaffolding of a lumen bifurcation 24, while also minimizing coverage of the carina 22. Thus, endoprostheses of the present invention can reduce or prevent damage to the carina such as, for example, stenosis in the case where the lumen is a diseased artery or other vessel. The endoprostheses of the present invention can provide these and other benefits due at least in part to a distal end that allows the endoprostheses to conform to the anatomy of the lumen bifurcation 24.

Figure 2A:
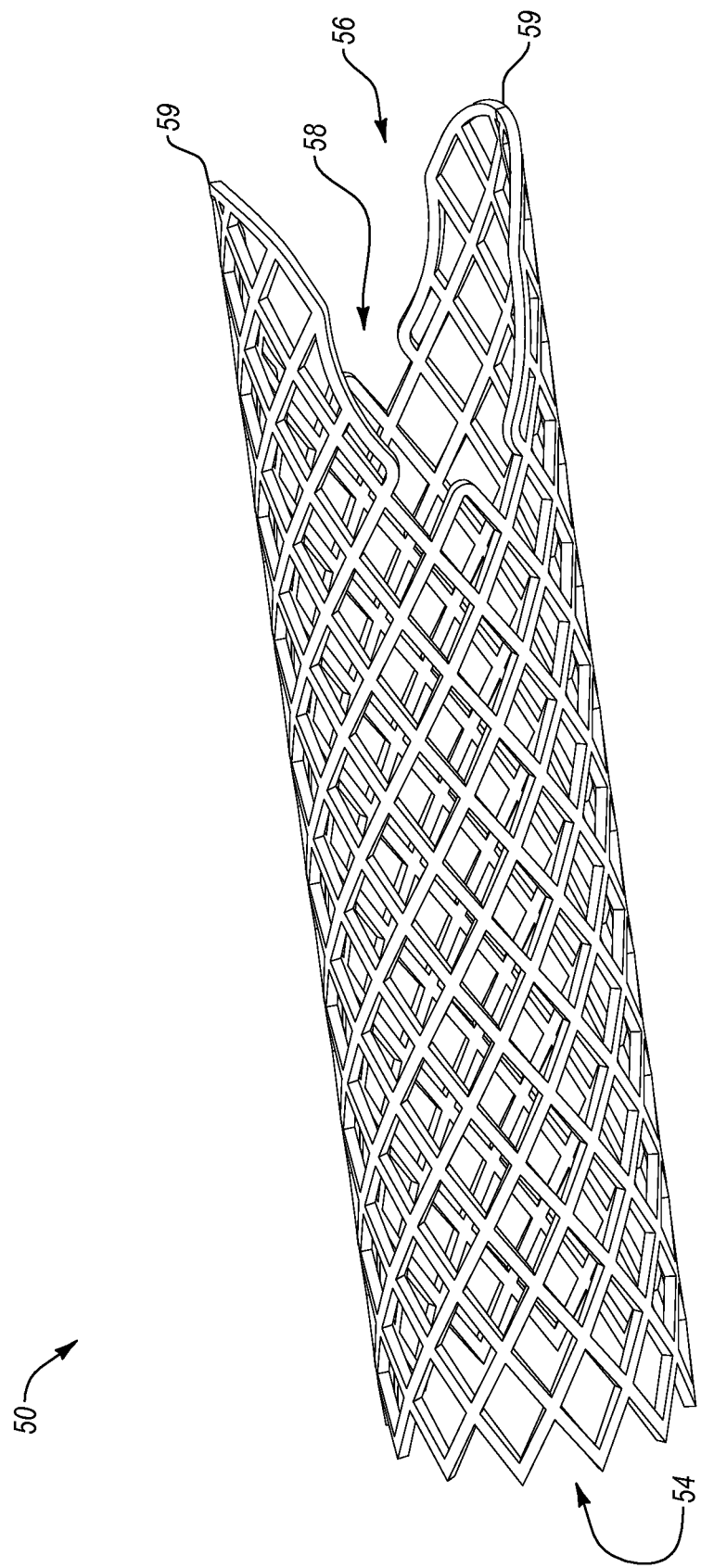
FIG. 2A is a perspective view of an endoprosthesis in an unexpanded configuration having a distal end with at least two wings and at least two troughs according to an implementation of the present invention.
Figure 2B:
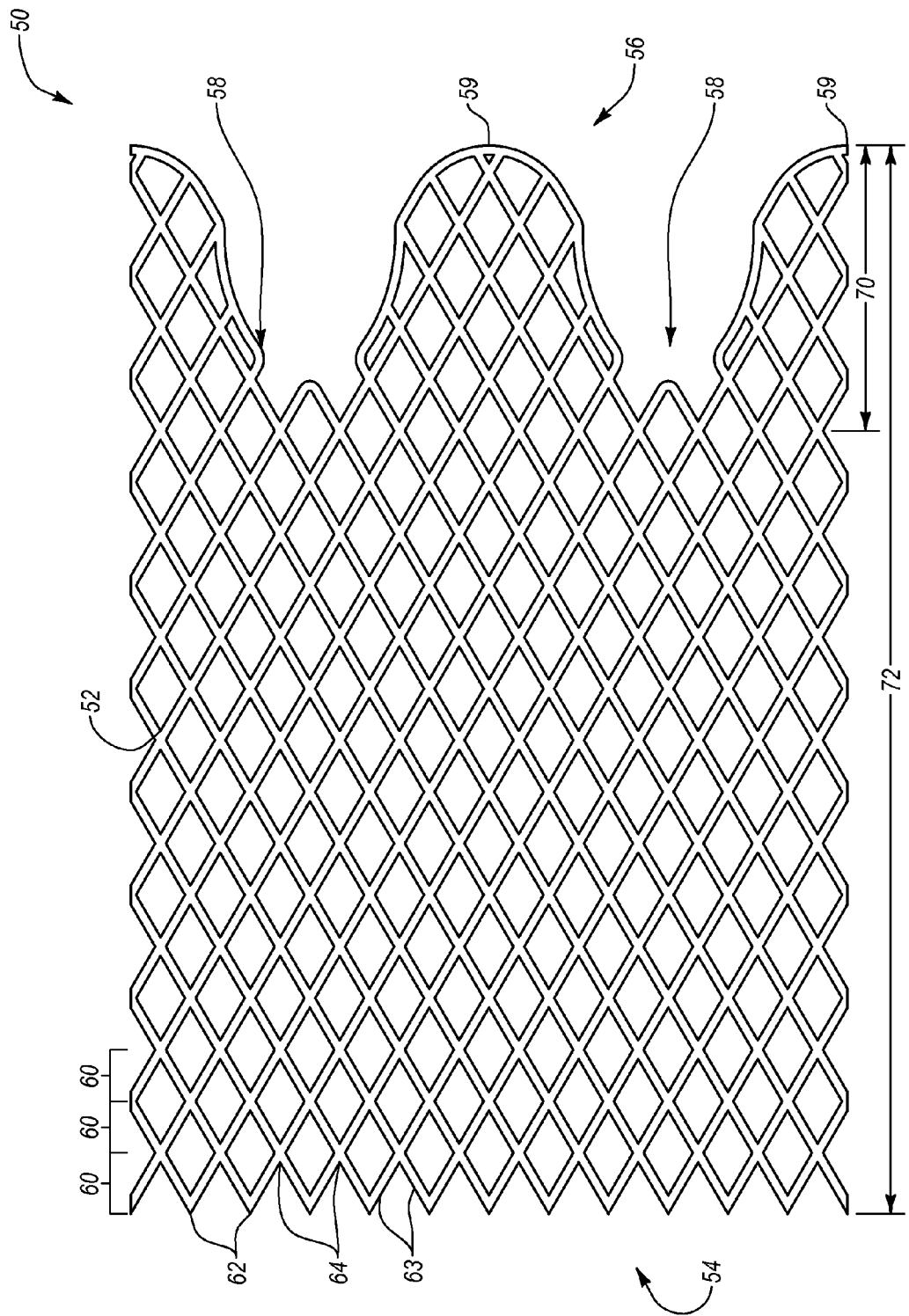
FIG. 2B is a flattened elevation view of the endoprosthesis of FIG. 2A.

For example, FIGS. 2A-2B depict an expandable endoprosthesis 50 in an unexpanded state, which is deployable for use at a lumen bifurcation 24, such as that shown in FIG. 1. In particular, FIG. 2A illustrates a perspective view of the endoprosthesis 50, while FIG. 2B illustrates a flattened, elevation view of the endoprosthesis 50. As shown in FIGS. 2A-2B, the endoprosthesis 50 can include a generally tubular body 52 formed from a plurality of interconnected concentric rings 60 aligned generally about the longitudinal axis of the endoprosthesis 50. One will appreciate that each concentric ring 60 can include a pattern or configuration that permits the endoprosthesis 50 to be radially compressed into delivery configuration having a first diameter, such as shown in FIGS. 2A-2B, and radially expanded to at least a deployment configuration having a second, larger diameter as explained in greater detail below.

Furthermore, the rings 60 of the endoprosthesis 50 can be configured to provide the endoprosthesis 50 with a relatively high degree of flexibility along its longitudinal axis, particularly when in the contracted or delivery configuration. This high degree of longitudinal flexibility can aid in delivery of the endoprosthesis 50 through curved and otherwise tortuous lumens. While the rings 60 can provide the endoprosthesis 50 with longitudinal flexibility, they also are sufficiently rigid and stable in the expanded or deployment configuration to maintain the patency of a lumen within which the endoprosthesis 50 is implanted.

As shown in FIGS. 2A-2B the cylindrical rings 60 can have a serpentine or undulating configuration formed from a plurality of crests 64 and valleys 62 connected by a plurality of strut elements 63. Furthermore, the valleys 62 of each concentric ring 60 can be at least partially offset from valleys 62 of each adjacent concentric ring 60. Similarly, the crests 64 of each concentric ring 60 can be at least partially offset from crests 64 of each adjacent concentric ring 60. Thus, as shown in FIGS. 2A-2B at least some of the valleys 62 of each concentric ring 60 can be at least partially aligned with and connected to some of the crests 64 of the adjacent concentric ring 60. According to some implementations of the present invention the crests 64 and valleys 62 of adjacent concentric rings 60 can be directly connected. For example, FIGS. 2A-2B illustrate that each crest 64 is directly connected to a valley 62 of an adjacent concentric ring 60 as shown in FIGS. 2A-2B. Such configurations can reduce or eliminate the tendency of the endoprosthesis 50 to "fishscale" (outward projection of some of the crests and/or valleys) when being bent or otherwise contorted during the implantation process.

According to some implementations of the present invention, the crests 64 and valleys 62 of concentric rings 60 can be indirectly connected. For example, as more fully described herein below, the endoprostheses of the present invention can include arm bars that indirectly connect adjacent concentric rings. The use of arm bars can provide the endoprostheses of the present invention with greater longitudinal flexibility and provide additional scaffolding.

The cylindrical body 52 of the endoprosthesis 50 can include a proximal end 54 and a distal end 56. As mentioned above, the distal end 56 of the endoprosthesis 50 can be configured to have increased expandability. For example, FIGS. 2A-2B show that the concentric rings 60 forming the distal end 56 of the endoprosthesis 50 can be arranged so the distal end 56 includes at least two recessed portions or troughs 58 and at least two protruding portions or wings 59. As shown in FIG. 5B, the peaks 59 can be formed from a web structure including a plurality of crests 64 and valleys 62. In other words, the wing portions 59 are larger than and include the crests 64 of the distal most concentric rings 60.

Additionally, as shown a recessed portion or trough 58 can extend between adjacent wings 59 so that the distal end 56 includes alternating wing 59 and recessed portions 58. One will appreciate in light of the disclosure herein that the at least two wings 59 and at least two troughs 58 can provide the distal end 56 of the endoprosthesis with increased expandability and flexibility. In particular, the at least two troughs 58 and the at least two wings 59 can allow the distal end 56 of the endoprosthesis 50 to flare out or extend radially outward farther than the proximal end 54 of the endoprosthesis 50.

The ability of the distal end 56 of the endoprosthesis 50 to flare out or extend radially outward farther than the proximal end 54 of the endoprosthesis 50 can help allow the endoprosthesis 50 to conform to the anatomy of a bifurcated lumen. For example, as explained in greater detail below, the ability of the at least two wings 59 to radially flare outward can help allow them to extend into and along the lateral walls of the side branches 16, 18 of a lumen bifurcation 24 (FIG. 1). Additionally, the ability of the distal end 56 of the endoprosthesis 50 to expand to a larger diameter can help allow the endoprosthesis 50 to extend around the carina 22 of a lumen bifurcation 24, and into the lumen side branches 16, 18 with little or no contact with the carina 22.

According to some implementations of the present invention, the wings 59 of the distal end of the endoprosthesis 50 can be formed by separating or removing portions of the rings 60 forming the distal end 56 of the endoprosthesis 50. Thus, as shown in FIGS. 2A-2B, the rings 60 forming the distal end 56 of the endoprosthesis 50 can include separated portions or segments. One will appreciate in light of the disclosure herein that because the rows of rings 60 of the distal end 56 of the endoprosthesis 50 are divided or separated by the troughs 58, the distal end 56 of the endoprosthesis 50 will be have increased flexibility. The increased flexibility of the wings 59 can help ensure that they are less resistant to radial loads applied by a pulsing lumen after deployment, and thus, help ensure that the wings 59 apply less stress on the lateral walls of the lumen side branches 16, 18 (FIG. 1). The increased flexibility of the distal end 56 of the endoprosthesis 50 may result in fewer traumas to the lumen side branches 16, 18 and a lower occurrence of restenosis in those areas.

The particular contour of the distal end 56 of the endoprosthesis 50 can be altered in shape and configuration from what is depicted in the Figures to correspond to the vascular anatomy of a lumen, bifurcated or not. For instance, according to some implementations of the present invention, the distal end 56 of the endoprosthesis 50 can include more than two troughs 58 and more than two wings 59. Thus, the endoprosthesis 50 can include, for example, three, four, five, or as many troughs 58 and wings 59 as needed to provide optimal scaffolding of a lumen. Additionally, the shape of the troughs 58 and wings 59 can be altered to correspond to the anatomy of a lumen. For example, the troughs 58 and wings 59 can be configured with a parabolic, elliptical, or other curvilinear or non-curvilinear shape. Thus, notwithstanding its characterization herein, it is appreciated that the endoprosthesis 50 can be configured in other ways from what is described herein while still residing within the scope of the claims.

Additionally, the depth 70 of each trough 58 can be sized to correspond to the anatomy of a lumen bifurcation and allow the endoprosthesis 50 to cover the ostium of a lumen bifurcation 24 with little or no contact with the carina 22. For example, according to some implementations of the present invention, the depth 70 of each trough 58 can be approximately one-fourth the length 72 of the endoprosthesis 50 or more. Alternatively, the depth 70 of each trough 58 can be between approximately one-third and approximately one-sixteenth of the length 72 of the endoprosthesis 50 or less. One will appreciate that the depth 70 of the troughs 58 can be based on the contour and shape of the carina 22 of a lumen bifurcation and on how much of the lumen side branches 16, 18 are to be covered by the scaffolding of the endoprosthesis 50. Thus, according to some implementations of the present invention, the depth 70 of each trough 58 may be approximately equal as shown in FIGS. 2A-2B. According to alternative implementations, however, the depths 70 of the troughs 58 may vary to allow the endoprosthesis 50 to conform to the anatomy of varying lumen bifurcations.

Similarly, the wings 59 of the distal end 56 of the endoprosthesis 50 can be configured in size and shape to correspond to the anatomy of a lumen bifurcation and/or the characteristics of a particular lesion being treated. Thus, according to some implementations of the present invention, each wing 59 of the distal end 56 of the endoprosthesis 50 can have approximately the same length as depicted in FIGS. 2A-2B. Alternatively, one or more of the wings 59 can have an increased length to allow the endoprosthesis 50 to extend to greater lengths along the lateral walls of a lumen side branch 16, 18 (FIG. 1). For example, when a lesion at a lumen bifurcation extends into and along the lateral wall of a lumen side branch 16, 18, the length of one of the wings 59 can be increased to ensure that the lateral side wall of the lumen side branch 16, 18 is adequately covered to prevent restenosis.

Additionally, the overall length 72 of the endoprosthesis 50 can be configured to correspond to the particular vascular anatomy of a patient or the particular characteristics of a lesion being treated. For example, according to some implementations of the present invention, the endoprosthesis 50 can have a length of about one millimeter to about fifty millimeters. According to additional implementations, the overall length 72 of the endoprosthesis 50 can be from about one-tenth a millimeter to about twenty-five millimeters or from about one-tenth a millimeter to about ten millimeters. One will appreciate in light of the disclosure herein, however, that these dimensions are exemplary only, and can change according to the patient, placement of the endoprosthesis 50, the lesion characteristics, or other factors.

As mentioned previously, the endoprostheses of the present invention can provide optimal scaffolding of a bifurcated lumen, while also preventing the traumatization of the carina. One will appreciate that this is due at least in part because the body 52 of the endoprosthesis 50 is monotubular. The monotubular configuration of the endoprosthesis 50a allows the carina 22 of a lumen bifurcation to extend at least partially into the lumen of the endoprosthesis 50. This is in contrast to many conventional endoprostheses for treating lumen bifurcations that include multiple tubular portions whose intersection abuts against the carina when deployed within a lumen bifurcation. The ability of the endoprostheses of the present invention to at least partially surround and only lightly touch, if at all, the carina of a lumen bifurcation helps prevent restenosis and other forms of damage to the carina.

The endoprostheses of the present invention are configured for use in a body lumen so as to adequately support and scaffold a region of a bifurcated lumen that has been diseased. As such, the present invention includes a method of delivering an endoprosthesis into a body lumen of a patient. Such a method can include: positioning a first guidewire within a main lumen of a patient proximate a lumen bifurcation and extending the first guidewire into a first lumen side branch; positioning a second guidewire within a main lumen of a patient proximate a lumen bifurcation and extending the second guidewire into a second lumen side branch; orienting an endoprosthesis as described herein into a delivery orientation by radially compressing the body of the endoprosthesis such that it has a diameter smaller than the diameter of the lumen within which it is to be deployed; affixing the endoprosthesis in the delivery orientation onto/into a delivery device, such as a balloon catheter or tubular catheter; delivering the endoprosthesis to a target deployment site on/within the delivery device by threading it along the first and second guidewires; and deploying the endoprosthesis at the lumen bifurcation such that it covers the portion of the main lumen 14 just prior to the lumen bifurcation, covers the ostium of the bifurcation by surrounding—but only lightly touching if at all—the carina 22, and covers at least the lateral walls of both of the lumen side branches 16, 18.

Figure 3A:
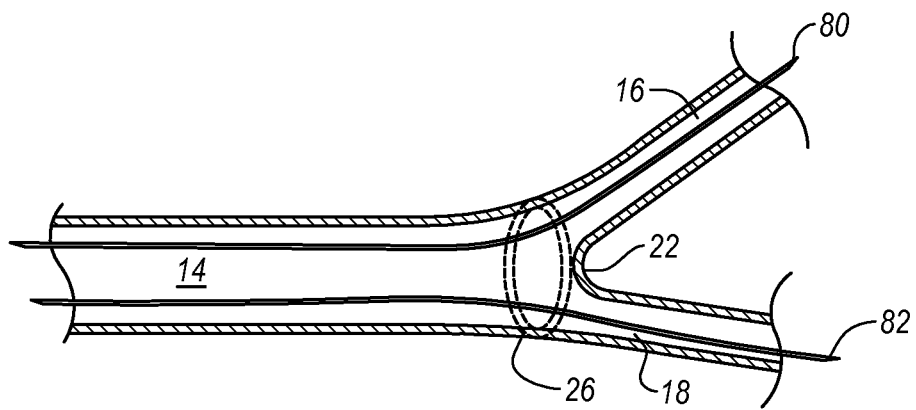
FIGS. 3A-3C depict various stages of a method of implanting the endoprosthesis of FIG. 2A at a lumen bifurcation according to an implementation of the present invention.
Figure 3B:
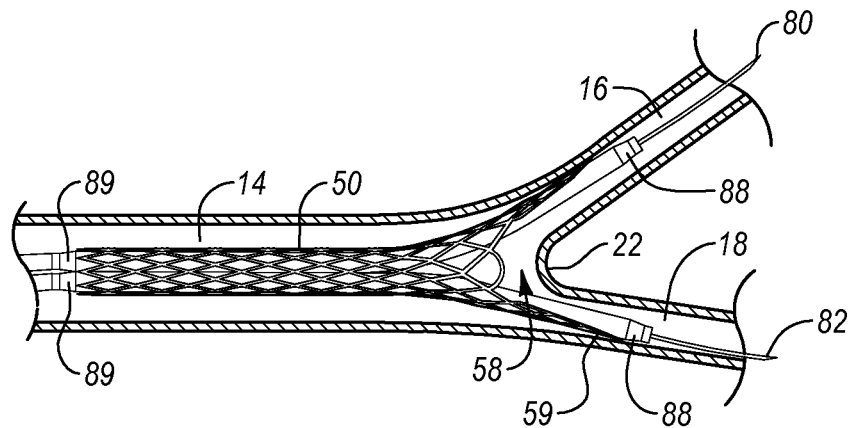
Figure 3C:
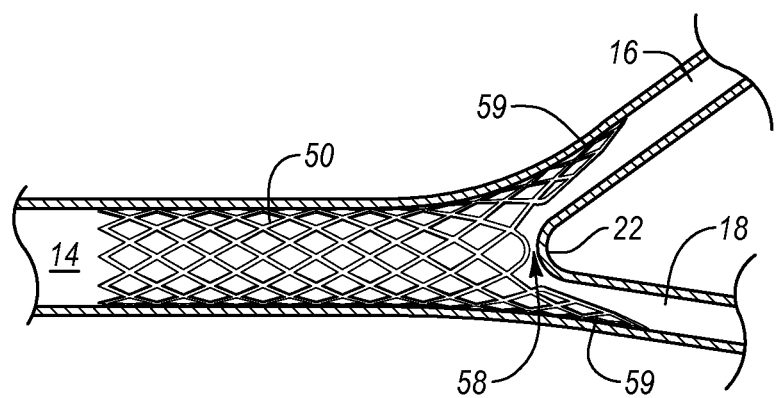

Reference is now made to FIGS. 3A-3C in describing various details regarding placement and deployment of the endoprosthesis 50 at a point of a lumen bifurcation according to an implementation of the present invention. Of course, as a preliminary matter, one of ordinary skill in the art will recognize that the methods explained in detail can be modified to deploy a wide variety of endoprostheses, within a wide variety of a bifurcated lumen, to treat a wide variety of lesions. For example, various acts of the method described can be omitted or expanded, and the order of the various acts of the method described can be altered as desired. Additionally, the endoprosthesis 50 described above in relation to FIGS. 2A-2B is depicted in FIGS. 3B-3C and is used in describing the methods of deployment of the present invention. The endoprosthesis 50, however, has only been used for ease in illustration. Thus, one will appreciate that the methods described herein can be used to deploy any of the endoprostheses shown in and described below in relation to FIGS. 4A-12B; or other endoprostheses not specifically described herein that fall within scope of the appended claims.

Thus, according to one method of the present invention, first and second guidewires 80, 82 can be positioned within a bifurcated lumen, as shown in FIG. 3A. In particular, a first guidewire 80 can be positioned within the main lumen 14 and extended past the lumen bifurcation into the first lumen side-branch 16. A second guidewire 82 can also be positioned within the main lumen 14 and extended past the lumen bifurcation into the second lumen side-branch 18.

After positioning of the first and second guidewires 80, 82, or before if desired, an endoprosthesis 50 can be oriented into a delivery orientation. Specifically, the endoprosthesis 50 can be radially compressed into a delivery configuration such that it has a diameter smaller that the diameter of the lumens 14, 16, 18 within which it will be deployed. Once the endoprosthesis 50 is compressed into a delivery configuration, it can be affixed to a delivery device. For example, the endoprosthesis 50, when balloon expandable, can be crimped upon a pair of balloon catheters as shown in FIG. 3B.

One will appreciate that the balloon catheters serve as only one example of a delivery device that can be used to deploy the endoprosthesis 50. Indeed, various other devices, such as mechanically expandable devices, may be acceptably employed as a means for selectively positioning and deploying the endoprosthesis 50 at a lumen bifurcation in accordance with the principles of the present invention. The present invention should therefore not be limited to any one embodiment. For example, when the endoprosthesis 50 is self-expanding, the delivery device can be a tubular catheter. In such instances, the endoprosthesis can be compressed into a delivery configuration and inserted with the lumen of the tubular catheter. The walls of the tubular catheter can then hold the endoprosthesis 50 in the delivery configuration and prevent the endoprosthesis 50 from expanding until desired.

In either case, once the endoprosthesis 50 has been affixed to a delivery device (e.g., balloon catheters or tubular catheter), it can be delivered to a target deployment site proximate a lumen bifurcation. For example, the balloon catheters can be tracked along the first and second guidewires 80, 82 until the trough(s) 58 of the endoprosthesis 50 are proximate the carina 22 of the lumen bifurcation as shown in FIG. 3B. One will appreciate that that the balloons of the balloon catheters are deflated during this phase of advancement through the lumen. When the trough(s) 58 of the endoprosthesis 50 are positioned proximate the carina 22 at the target deployment site, a first wing 59 of the endoprosthesis 50 may extend at least partially into the first lumen side branch 16 and a second wing 59 of the endoprosthesis 50 may extend at least partially into the second lumen side branch 18 as shown in FIG. 3B.

The endoprosthesis 50 can be delivered to the target deployment site within a tubular catheter. In particular, the tubular catheter can be threaded along the first and second guidewires 80, 82 until the trough(s) 58 of the endoprosthesis 50 are proximate the carina 22. Furthermore when at the target deployment site, a first wing 59 of the endoprosthesis 50 can extend at least partially into the first lumen side branch 16, and a second wing 59 of the endoprosthesis 50 can extend at least partially into the second lumen side branch 18 as shown in FIG. 3B. One will appreciate in light of the disclosure herein that the first and second guidewires 80, 82 can be used to guide and place at least a portion of the wings 59 within the first and second side branches 16, 18.

To aid in delivering and positioning the endoprosthesis 50 at the target deployment site in the proper orientation the delivery device can include position indicators or markers 88, 89 adjacent its longitudinal ends. The markers can indicate the position of the delivery device within a lumen when viewed radiographically. In the present embodiment, the position indicators are implemented as annular, radiopaque ("RO") bands that are disposed about the outer surface of the both ends of the delivery device. One will appreciate that other suitable port position indicators could alternatively be implemented in other implementations. The RO bands 88, 89 are composed at least partially of a radiopaque material, including metals such as platinum, tungsten, silver, stainless steel, gold, tantalum, bismuth, barium sulfate and alloys thereof, plastics, polymers, other synthetic materials, etc.

As shown in FIG. 3B, the RO bands can include a proximal pair 89 and a distal pair 88. Furthermore, the wings 59 of the endoprosthesis 50 can be positioned on the delivery device such that they are proximate the distal markers 88. Thus when positioning the endoprosthesis 50, the distal markers 88 can be used to ensure that the wings 59 of the endoprosthesis 50 extend at least partially into the first and second lumen side branch 16, 18.

Moreover, the endoprosthesis 50 can include radiopaque material to increase visibility during placement. Optionally, the radiopaque material can be a layer or coating on any portion of the endoprosthesis 50. The radiopaque materials can be platinum, tungsten, silver, stainless steel, gold, tantalum, bismuth, barium sulfate, and alloys thereof, plastics, polymers, other synthetic materials, etc. Also radiopaque material can be encapsulated within a biocompatible or biodegradable polymer and used as a coating. The radiopaque material can be applied as layers on selected surfaces of the endoprosthesis 50 using any of a variety of techniques, including cladding, bonding, adhesion, fusion, deposition or the like.

Thus according to some implementations of the present invention, at least the portion of the endoprosthesis 50 surrounding the troughs 58 can include a radiopaque material to increase visibility of the troughs 58 during placement. The increased visibility provided by including radiopaque material in at least the portion of the endoprosthesis 50 surrounding the troughs 58 can help in positioning the troughs 58 proximate the carina 22, with little or no contact of the carina 22.

Once the endoprosthesis 50 is positioned at the target deployment site as shown in FIG. 3B—with the trough(s) 58 proximate and at least partially surrounding the carina 22, the first wing 59 of extending at least partially into the first lumen side branch 16, and the second wing 59 extending at least partially into the second lumen side branch 18—the endoprosthesis 50 can be deployed. For example, the balloons of the balloon catheters can be inflated to cause the endoprosthesis 50 to radially expand outward toward the walls of the lumens 14, 16, 18. Indeed, inflation of the balloons can cause the endoprosthesis 50 to expand such that it seats against the wall of the main lumen 14 and the lateral sides of the walls of the first and second lumen side branches 16, 18, as shown in FIG. 3C.

Alternatively, when the endoprosthesis 50 is self-expanding, it can be deployed by pushing the endoprosthesis 50 out of the lumen of the tubular catheter into the desired implantation site as depicted in FIG. 3C. In particular, once at the deployment site, the endoprosthesis 50 can be pushed out of the distal end of the tubular catheter by using a pusher or other tool to push on the proximal end 54 of the endoprosthesis 50. In alternative implementations, the endoprosthesis 50 can be disposed at the distal end of the tubular catheter, and a pusher or other tool can hold the endoprosthesis 50 at the target deployment site while a sleeve of the tubular catheter is retracted from over the endoprosthesis 50. In either case, once the endoprosthesis 50 has been removed from the tubular catheter, it automatically expands radially from the delivery configuration (FIG. 3B) to the deployment configuration (FIG. 3C) so as to contact the inner walls of the main lumen 14 and lumen side branches 16, 18.

Once the endoprosthesis 50 is fully expanded into the deployment configuration, the delivery device and the guidewires 80, 82 can be withdrawn from the lumen 10. For example, the balloons of the balloon catheters can be deflated and pulled from the lumen 14, 16, 18, leaving the endoprosthesis 50 expanded at the lumen bifurcation as shown in FIG. 3C.

As shown in FIG. 3C, when positioned and expanded at the lumen bifurcation, the endoprosthesis 50 can scaffold the lumen bifurcation by covering the portion of the main lumen 14 just prior to the lumen bifurcation, covering the ostium 26 of the bifurcation by surrounding—but only lightly touching if at all—the carina 22, and covering at least the lateral walls of both of the lumen side branches 16, 18. In particular, as shown in FIG. 3C the troughs 58 of the distal end 56 of the endoprosthesis 50 allow the carina 22 to be at least partially inserted within the lumen of the endoprosthesis 50. The increased proximity of the endoprosthesis 50 to the carina 22 allows the wings 59 to extend further along the lateral walls of the lumen side branches 16, 18. Furthermore, the increased expandability of the distal end 56 of the endoprosthesis 50 allows it to expand radially outward enough to adequately cover portions of the ostium 26 of the lumen bifurcation despite their increased diameter. Thus, the endoprosthesis 50 can provide optimal scaffolding of the bifurcated lumen, while also preventing the traumatization of the carina 22.

Furthermore, one will appreciate in light of the disclosure herein that the distal end 56 of the endoprosthesis 50 can be configured in size and shape such that when deployed proximate a bifurcated lumen, as shown in FIG. 3C, the troughs 58 can straddle the carina 22 of the bifurcated lumen. Additionally, the distal end 56 of the endoprosthesis 50 can be configured in size and shape so when deployed the at least two wing portions can extend into and along the lateral walls of the side branches 16, 18 of the bifurcated lumen.

In addition to the wings 59 and troughs 58, the distal ends of the endoprostheses of the present invention can include additional characteristics and features to provide them with increased expandability and flexibility. For example, according to some implementations of the present invention the rings 60 forming the distal end 56 of the endoprostheses can be thinner than the rings 60 forming the proximal end 54 of the endoprostheses. The reduced gauge or thickness of the rings 60 forming the distal ends 56 of the endoprostheses can provide them with greater flexibility and expandability.

Figure 4A:
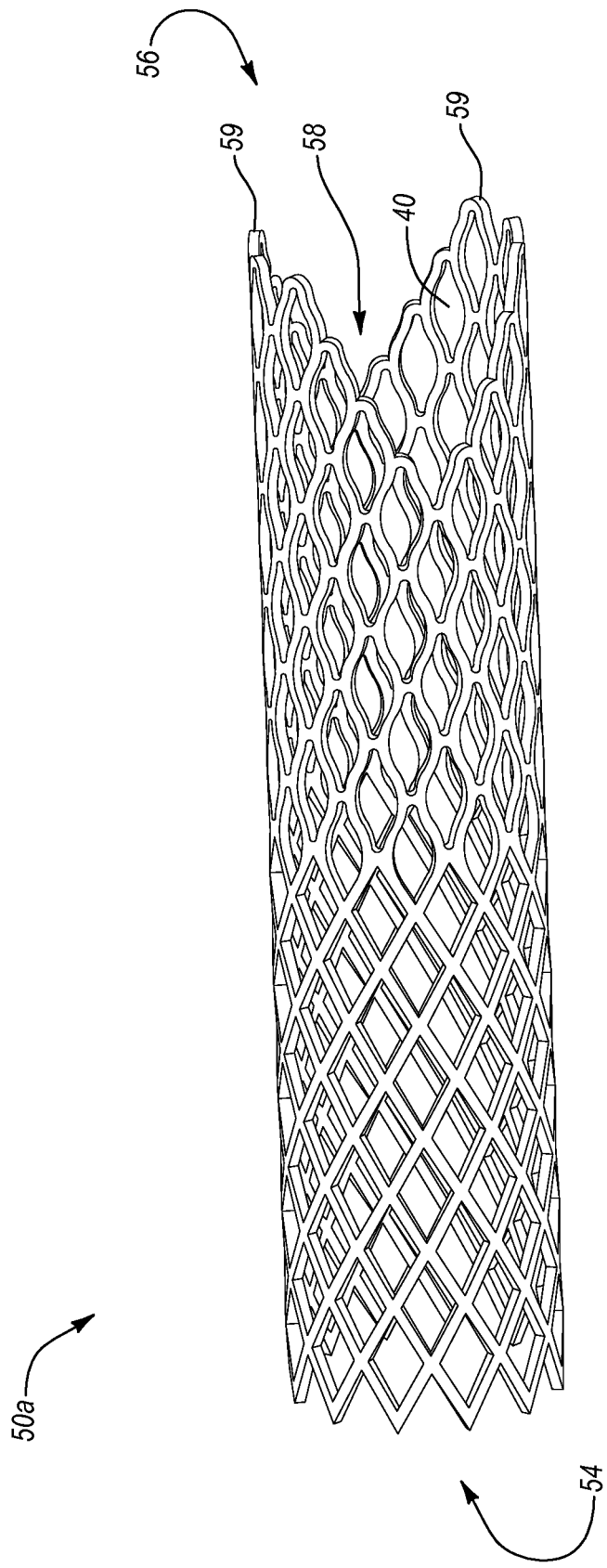
FIG. 4A is a perspective view of an endoprosthesis in an unexpanded configuration having a distal end with walnut shaped cells according to an implementation of the present invention.
Figure 4B:
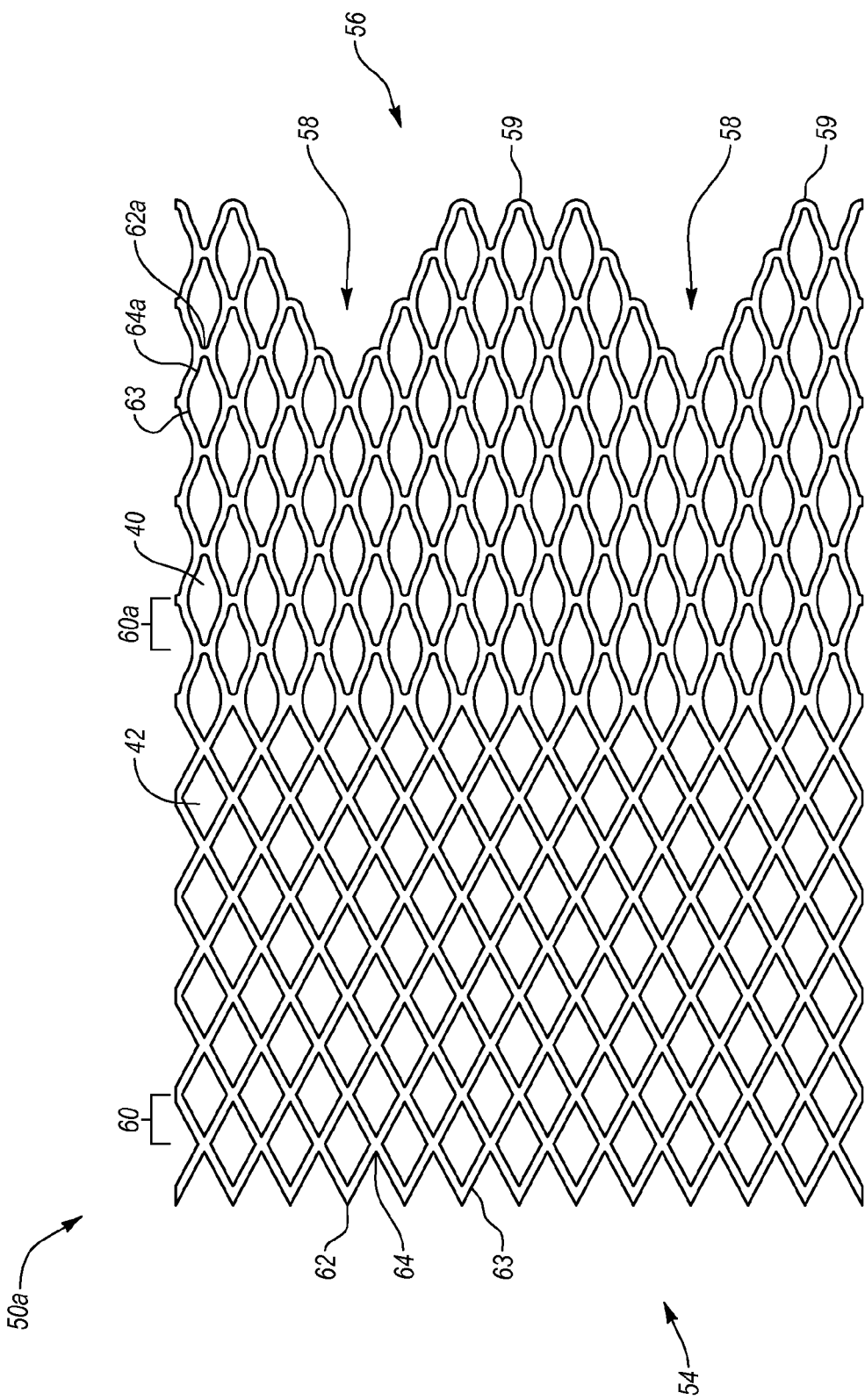
FIG. 4B is a flattened elevation view of the endoprosthesis of FIG. 4A.

Additionally, the configuration or pattern of the rings 60 forming the distal end 56 of the endoprostheses of the present invention can be modified or varied to provide them with increased expandability and flexibility. For instance, FIG. 4A illustrates a perspective view and FIG. 4B illustrates a flattened, elevation view of an endoprosthesis 50a where the rings 60a forming distal end 56 of the endoprosthesis 50a have a configuration or pattern that provides the distal end 56 of the endoprosthesis 50a with increased radial expandability. As shown in FIGS. 4A-4B, the crests 64a and the valleys 62a forming the rings 60a of the distal end of the endoprosthesis 50a can be contoured. In particular, both the apices of the crest 64a and the valleys 62a can be curved to form a knob like structure. In other words, each apex of each ring 60a of the distal end 56 of the endoprosthesis 60a can have a semi-circular shape. Furthermore, the strut elements 63a connecting adjacent crests 64a and valleys 62a can also be curved. Thus, when adjacent rings 60a are interconnected they can form walnut-shaped cells 40 as shown in FIGS. 4A-4B.

The walnut-shaped cells 40 of the distal end 56 of the endoprosthesis 50a can provide greater expansion than the diamond-shaped cells 42 of the proximal portion of the endoprosthesis 50a. In particular, the semi-circular apices and the curved strut elements 63a connecting the apices can allow the interconnected rings 60a to compress to smaller diameters and expand to greater diameters. Thus, the walnut-shaped cells 40 of the distal end 56 of the endoprosthesis 50a can allow the endoprosthesis 50a to extend radially outward enough to sufficiently scaffold the regions of a lumen bifurcation with increased diameter, such as the ostium. Furthermore, because the wings 59 of the distal end 56 are formed from walnut-shaped cells 40, the wings 59 can expand to scaffold a greater area of the lateral walls of the lumen side branches within which they are implanted.

One will appreciate in light of the disclosure herein that the rings of the endoprostheses of the present invention can be designed to have various different configurations and patterns to provide the distal ends of the endoprostheses with increased expandability. Thus, according to some implementations of the present invention the rings of at least the distal end of the endoprosthesis can be angled to form a wave pattern to increase flexibility and improve the ability of the distal end of the endoprostheses of the present invention to conform to the anatomy of a bifurcated lumen.

Figure 5A:
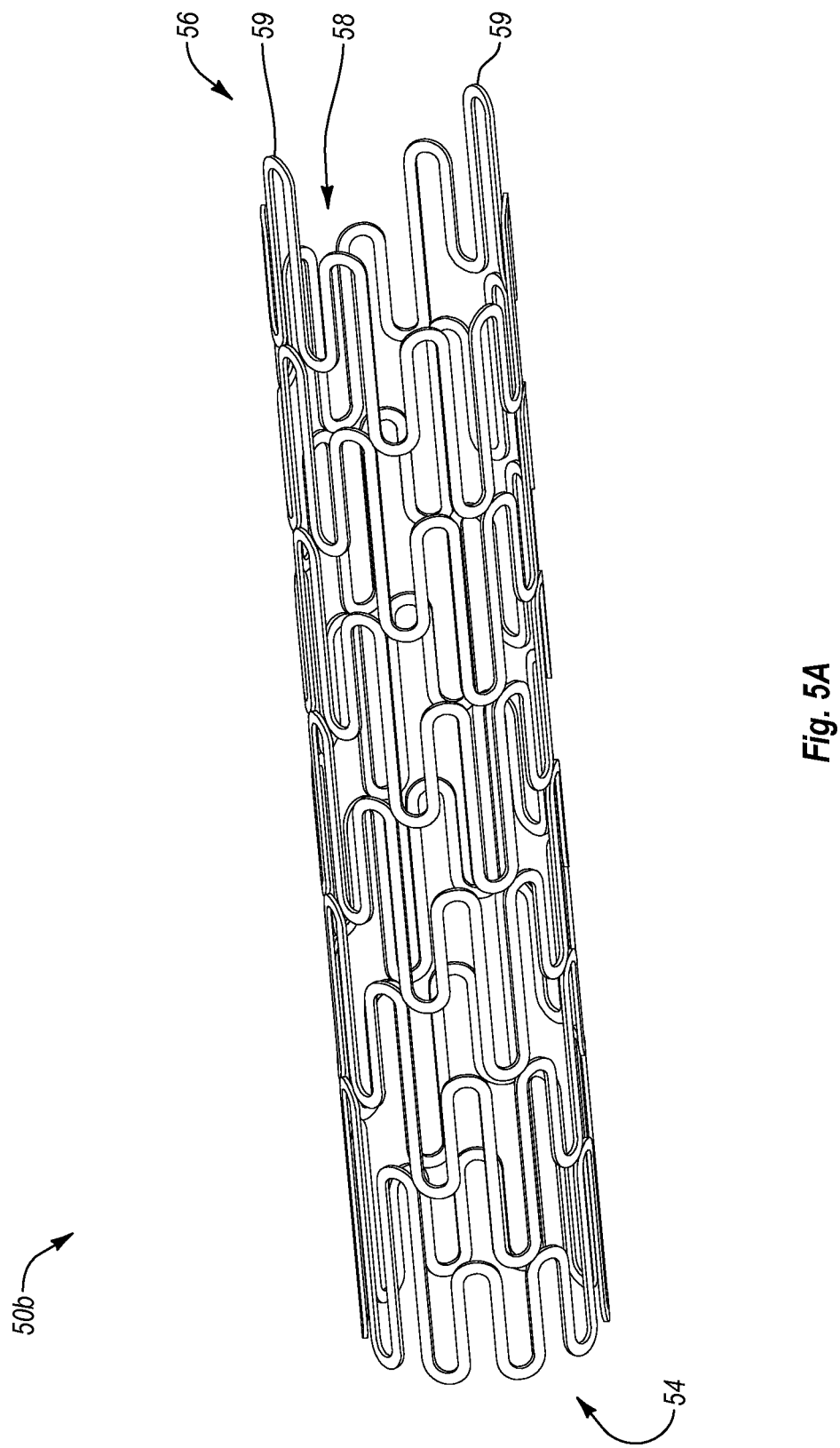
FIG. 5A is a perspective view of an endoprosthesis in an unexpanded configuration having a distal end with cells aligned in a wave pattern according to an implementation of the present invention.
Figure 5B:
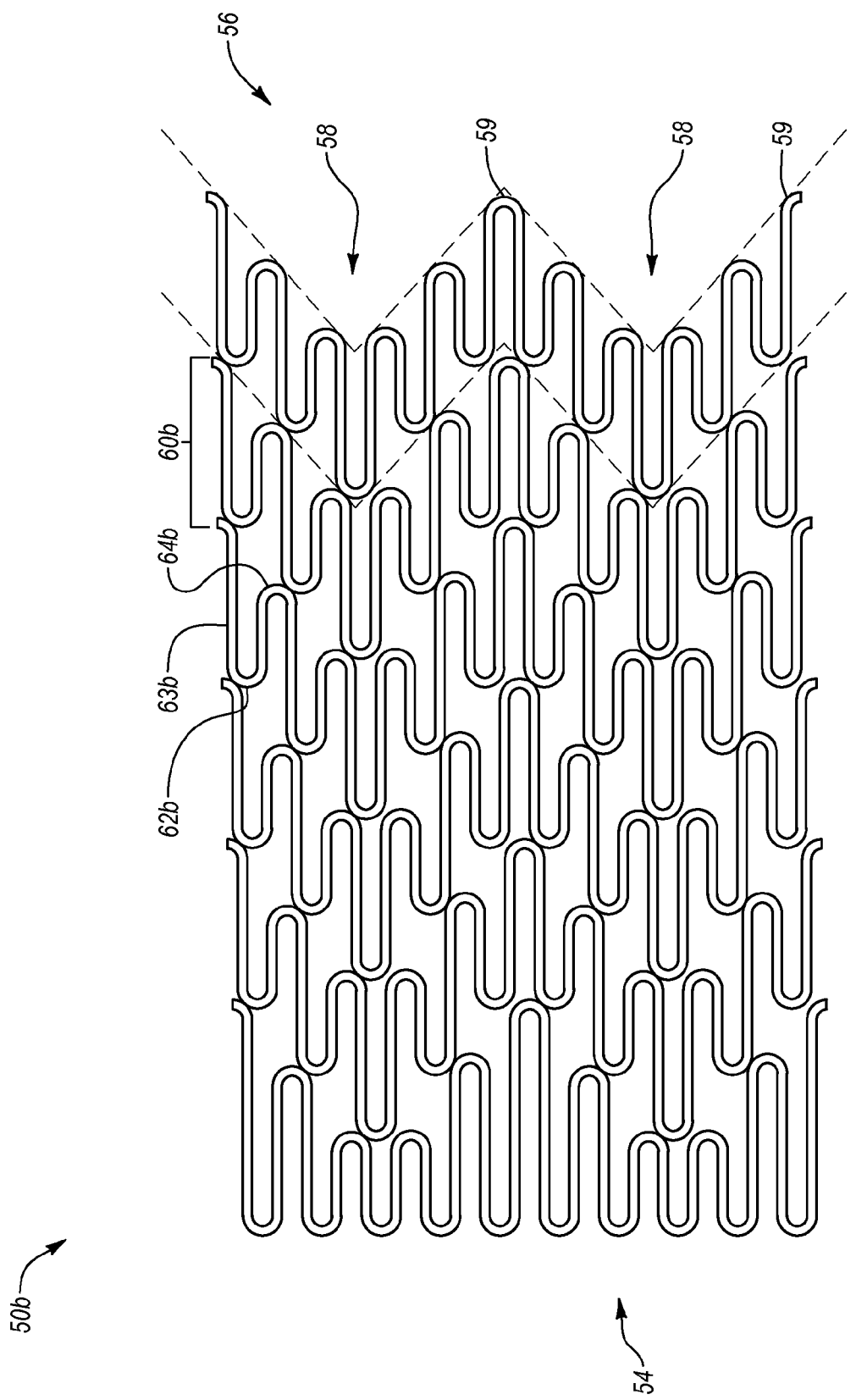
FIG. 5B is a flattened elevation view of the endoprosthesis of FIG. 5A.

For example, FIG. 5A illustrates a perspective view and FIG. 5B illustrates a flattened, elevation view of an endoprosthesis 50b having a distal end 56 formed from angled rings 60b. In particular, the crests 64b and valleys 62b of the distal most rings 60b can be aligned in wave like pattern. Thus, as shown by the dashed lines of FIG. 5B, a wave pattern can be formed by arranging the crests 64b of at least the distal end 56 in a pattern of increasing and decreasing distal extent. The crests 64b having an increased distal extension can form the peaks of the wave pattern, and the crests 64b having a decreased distal extension can form the troughs of the wave pattern.

As shown in FIG. 5B, the concentric rings 60b of the distal end 56 which are aligned in a wave pattern can at least partially define the wing portions 59 and the recessed portions or troughs 58. In particular, the peaks of the wave pattern can at least partially define the wing portions 59. Similarly, the valley or troughs of the wave pattern can at least partially define the recessed portions 58. Thus, one will appreciate that the crests 64b with increased distal extension can form the wings 59 of the distal end 56, while the crests 64b having a decreased distal extension can help form the recesses or troughs 58 of the distal end 56 of the endoprosthesis 50b. According to some implementations of the present invention, the valleys 62b of the rings 60b forming the distal end 56 can also be arranged in a pattern of increasing and decreasing extent to form the wave pattern. One will appreciate in light of the disclosure herein, that the wave pattern of the distal rings 60b can help increase the flexibility of the distal end 56 of the endoprosthesis 50b, and help the distal end 56 of the endoprosthesis 50b to better conform to the anatomy of a bifurcated lumen.

According to some implementations of the present invention, the wave pattern can be formed by varying the length of the stent elements 63b connecting the crests 64b and valleys 62b of the concentric rings 60b. For example, the strut elements 63b can have alternating longer and shorter lengths, with a pair of longer strut elements 63b connecting the distal and proximal most apices of the concentric rings 60b.

In addition to arranging the crests 64b of the rings 60b forming the distal end 56 of the endoprosthesis in a wave like pattern, the number of crest forming the distal most ring of the endoprosthesis 50b can be configured to help allow the endoprosthesis 50b conform to anatomy of bifurcated lumen. For example, the number of crests 64b in the rings 60b of the distal end 56 of the endoprosthesis 50b can large enough to ensure the scaffolding has adequate radial strength, but small enough to allow the individual crests to flex and otherwise conform to the anatomy of a bifurcated lumen. Thus, as FIGS. 5A-5B illustrate the rings 60b forming the distal end 56 of the endoprosthesis 50b can include ten crests 64b. One will appreciate, however, that the number of crests 64b can be increased or decreased from ten to help allow the endoprosthesis 50b to conform to a lumen bifurcation. For example, according to some implementations of the present invention the rings 60b forming the distal end 56 of the endoprosthesis 50b can include between six and twenty crests 64b. Alternatively, the rings 60b forming the distal end 56 of the endoprosthesis 50b can include less than six crests 64b or more than twenty crests 64b.

As mentioned previously, the distal end 56 of the endoprostheses of the present invention can include increased expandability to allow them to provide optimal scaffolding of a bifurcated lumen, while also preventing the traumatization of the carina. In particular, the distal ends of the endoprostheses can be designed to expand radially outward farther than the proximal ends. The increased radial expansion allows the endoprostheses of the present invention to sufficiently scaffold the portions of a lumen bifurcation that have increased diameter. Additionally, the increased radial expansion can help allow the distal end of the endoprostheses of the present invention to at least partially surround the carina of a lumen bifurcation to prevent damage thereto. According to some implementations of the present invention, the ability of the distal end of an endoprosthesis of the present invention to expand can be increased by decoupling it as much as possible from the proximal portion of the endoprosthesis.

Figure 6A:
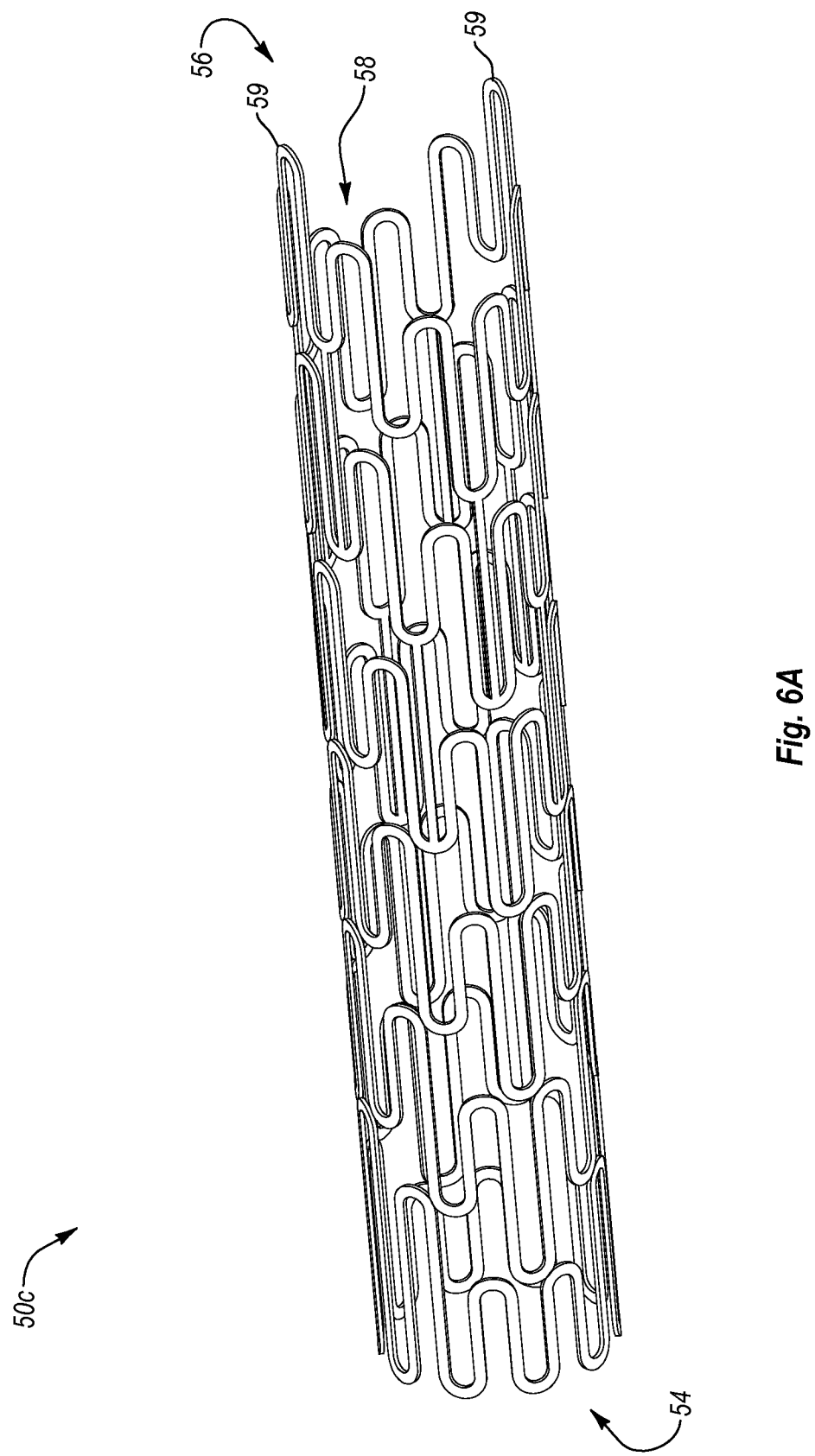
FIG. 6A is a perspective view of an endoprosthesis in an unexpanded configuration having arm bars connecting the distal cell rows according to an implementation of the present invention.
Figure 6B:
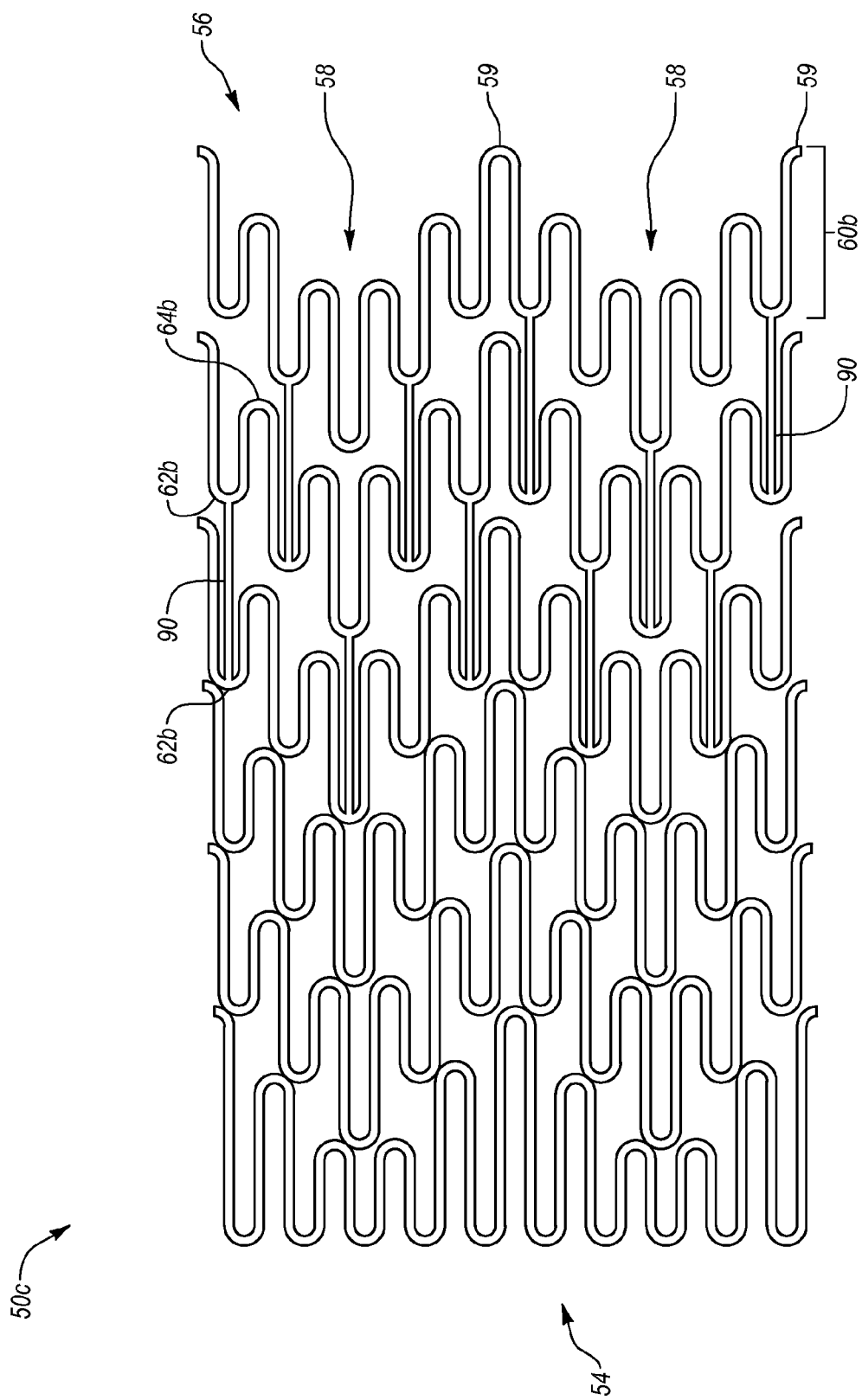
FIG. 6B is a flattened elevation view of the endoprosthesis of FIG. 6A.

As shown in FIGS. 6A-6B, according to some implementations of the present invention, the rings 60b forming the distal portion 56 of an endoprosthesis 50c can be decoupled from the proximal portion 54 by a plurality of inter-connectors 90. For example, at least the two distal-most rings 60b of the endoprosthesis 50c can be connected to each other and to the proximal portion 54 of the endoprosthesis 50c by a plurality of inter-connectors 90. The inter-connectors 90 can be flexible and allow the distal portion 56 of the endoprosthesis 50c to be highly flexible along its longitudinal axis. For instance, the positioning of the inter-connectors 90 can enhance the flexibility of the endoprosthesis 50c by allowing uniform flexibility when the endoprosthesis 50c is twisted or bent along its longitudinal axis. The longitudinal flexibility of the endoprosthesis 50c can be due in part at least to the staggering of the inter-connectors 90. In particular, the inter-connectors 90 on either side of a concentric ring 60b can be circumferentially offset from each other. While the rings 60 and inter-connectors 90 are generally not separate structures, they have been referred to as such for ease of description.

As shown in FIG. 6B, four inter-connectors 90 can secure each ring 60b of the distal portion 56 to an adjacent ring 60b. The number of inter-connectors 90 that interconnect adjacent rings 60b; however, can be varied to increase or decrease the flexibility of the endoprosthesis 50c. Thus, each ring 60b of the distal end 56 can be secured to an adjacent ring 60b by at least one inter-connector 90, but more if desired. Since the inter-connectors 90 typically do not expand when the rings 60 of the endoprosthesis 50c expand radially outward, the inter-connectors 90 can continue to provide flexibility and scaffolding of a lumen.

Additionally, the location of inter-connectors 90 that interconnect adjacent rings 60b can be varied. For example, FIG. 6B illustrates that at least a portion of each inter-connector 90 can be positioned within one of the valleys 62b and can attach to an apex of a valley 62b of an adjacent row 60b. According to other implementations of the present invention; however, at least a portion of each inter-connector 90 can be positioned within one of the crest 64b and can attach it to an apex of a crest 64b of an adjacent row 60b. Alternatively, the inter-connectors 90 can secure the valleys 62b of one row 60b to the crests 64b of an adjacent row 60b. For example, the inter-connectors 90 can be positioned within at least a portion of a valley 62b of one ring 60b and within at least a portion of a crest 64b of another ring 60b.

Figure 7A:
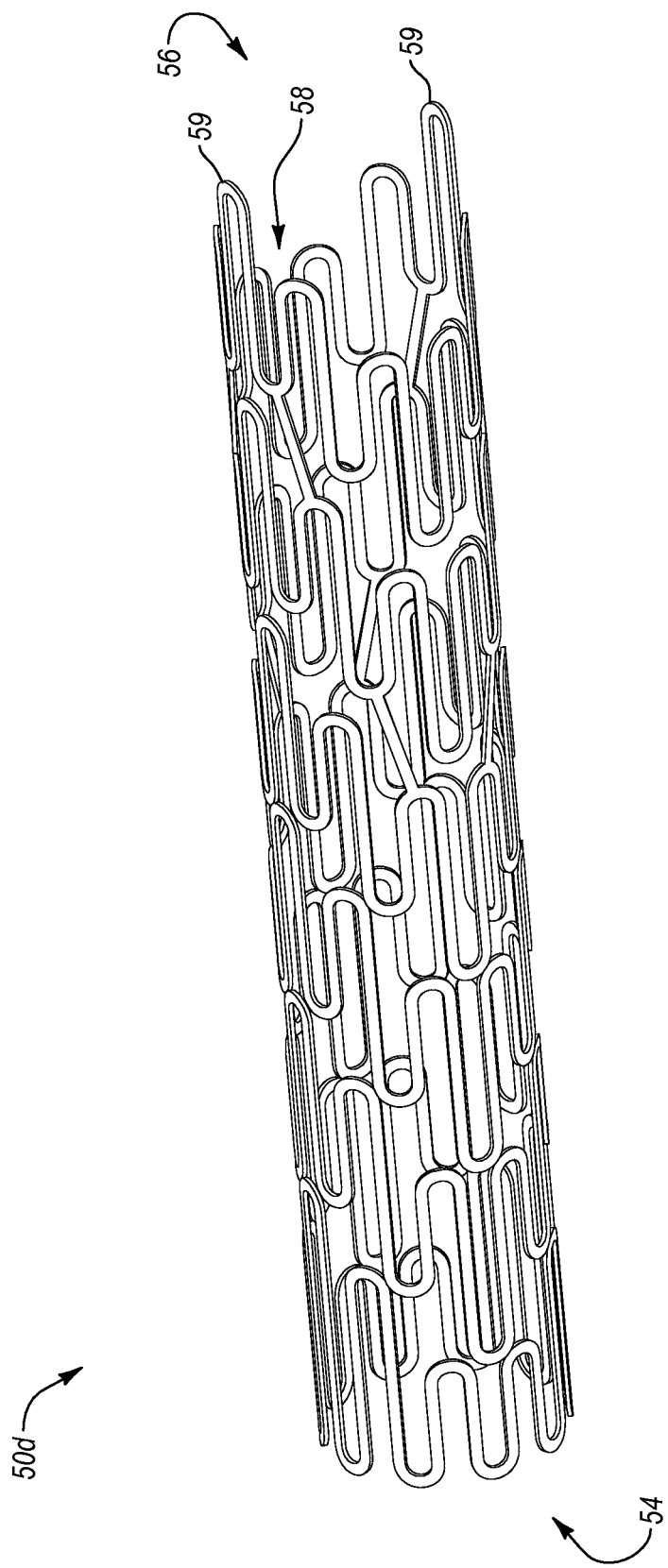
FIG. 7A is a perspective view of an endoprosthesis in an unexpanded configuration having angled arm bars connecting the distal cell rows according to an implementation of the present invention.
Figure 7B:
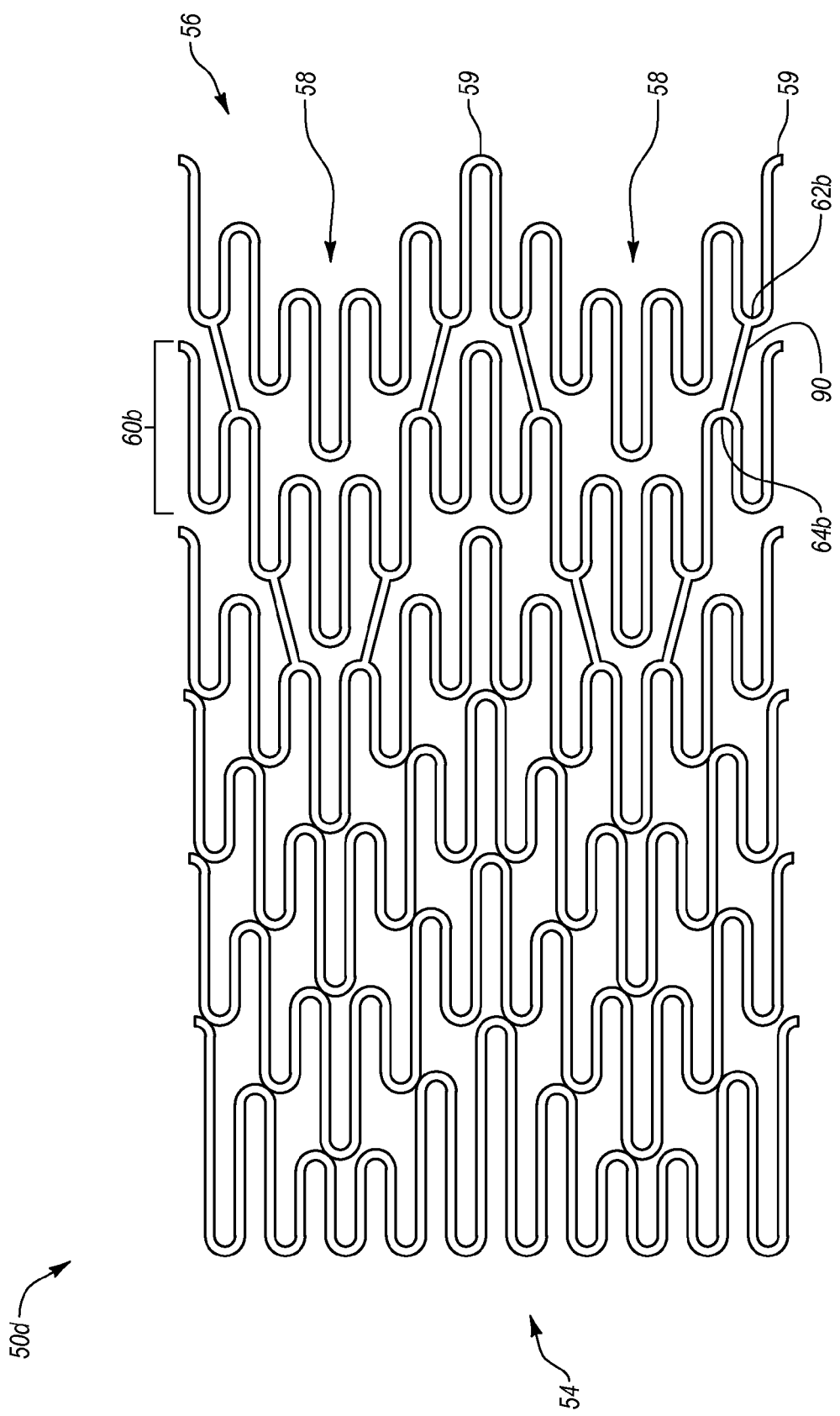
FIG. 7B is a flattened elevation view of the endoprosthesis of FIG. 7A.

One will appreciate in light of the disclosure herein, that the orientation of the inter-connectors 90 can also be varied. For example, the inter-connectors 90 depicted in FIGS. 6A-6B each extend in a direction substantially parallel with the longitudinal axis of the endoprosthesis 50c. The inter-connectors 90 can also be angled, however, as illustrated by FIGS. 7A-7B. In particular, FIGS. 7A-7B illustrate that the inter-connectors 90 can connect apices of the crests 64b of one row 60b with the apices of the valleys 62b of an adjacent row 60b. The angled inter-connectors 90 can provide the distal portion 56 with even more flexibility than that provided by straight inter-connectors. In particular, the angled inter-connectors 90 can provide with distal portion 56 of the endoprosthesis 50d with increased radial expandability and flexibility.

Additionally as shown in FIG. 7B, the angled inter-connectors 90 can be oriented or aligned in a manner to help decouple the wings 59 form the proximal portion 56 of the endoprosthesis as much as possible. Thus, the angled inter-connectors 90 can be secured between the crests 64b and the valleys 62b forming the wings 59 or peaks of the wave pattern.

Figure 8A:
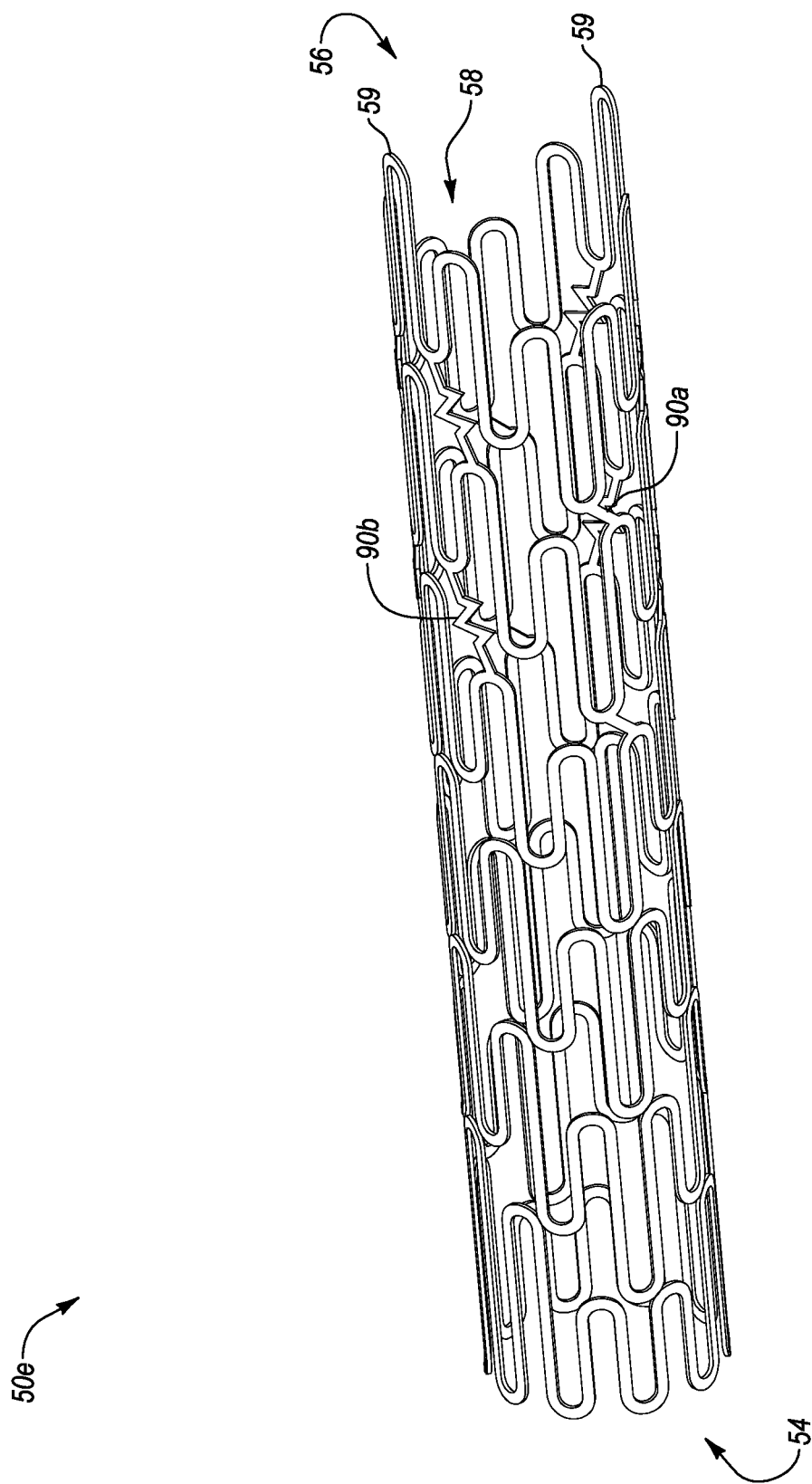
FIG. 8A is a perspective view of an endoprosthesis in an unexpanded configuration having expandable arm bars connecting the cells forming wings in the distal end of the device according to an implementation of the present invention.
Figure 8B:
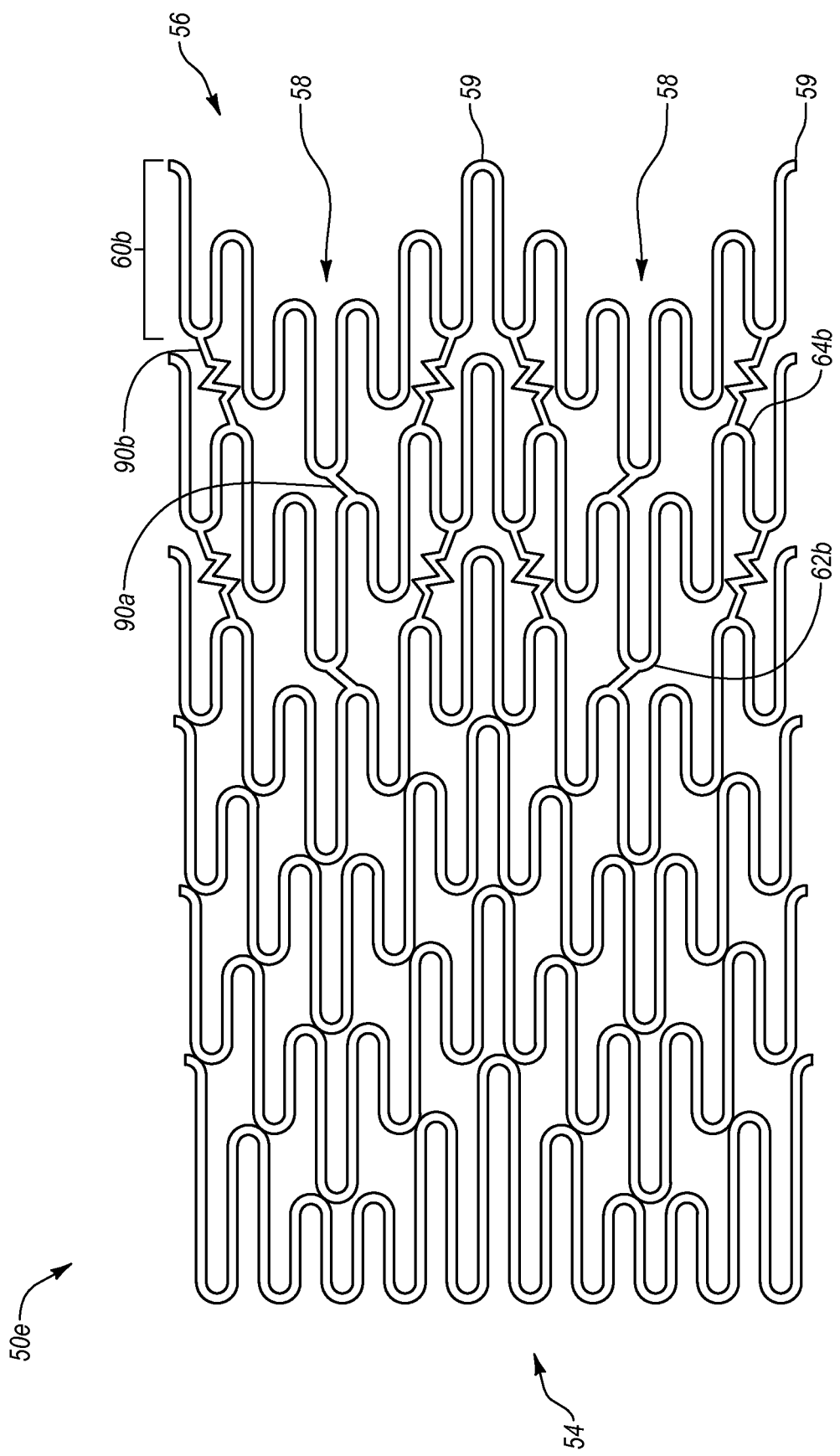
FIG. 8B is a flattened elevation view of the endoprosthesis of FIG. 8A.

In addition to decoupling the distal portion 56 of the endoprosthesis 50d from the proximal end 54 and thereby providing the distal end 56 with increased expandability and flexibility, the inter-connectors 90 can also be used to help prevent the endoprosthesis 50d from contacting the carina of a bifurcated lumen. For example, FIGS. 8A-8B illustrate shorter inter-connectors 90a can be used to connect the crests 64b and valleys 62b forming the troughs 58. The shorter inter-connectors 90 can at least partially restrict the longitudinal extension of the troughs 58, when compared with the wings 59, to help prevent the troughs 58 from contacting the carina of a lumen bifurcation when deployed therein.

FIGS. 8A-8B also illustrate that the crests 64b and valleys 62b forming the wings 59 can be connected by expandable inter-connectors 90b. As shown by FIGS. 8A-8B, the expandable inter-connectors 90b can include a series of angles or coils in the contracted configuration. The angles or coils can be pulled or straightened out when the endoprosthesis 50e is expanded into the deployment configuration. Thus, the expandable inter-connectors 90b provide the distal end 56 of the endoprosthesis, and particularly the wings 59, with increased longitudinal expandability. The increased longitudinal expandability can allow the wings 59 to extend distally into the side branches of a lumen bifurcation. Furthermore, the expandable inter-connecters 90b can provide the wings 59 with greater radial expandability by further decoupling the wings 59 from the proximal portion 54 of the endoprosthesis 50e.

According to additional implementations of the present invention, the inter-connectors 90 can include a series of coils or angles, similar to those of the expandable inter-connecters 90b, which are not expandable. Instead of helping to provide increased longitudinal expandability, the coils or angles of the inter-connectors 90 can provide additional scaffolding. In particular, the use of inter-connectors 90 to secured adjacent rings 60 together creates a gap between the rings. This gap thus creates an area of the endoprosthesis with reduced scaffolding ability. Thus, the inter-connectors 90 can include angles or coils that extend into these gaps and provide the endoprosthesis with greater scaffolding ability.

While the each of the exemplary endoprostheses described herein above has included a distal portion 56 that is designed with a configuration and/or pattern differing from the proximal portion 54, the present invention is not so limited. Indeed, according to some implementations of the present invention the entire endoprosthesis can include a similar pattern. For example, FIGS. 9A-9B illustrate an endoprosthesis 50f in which both the distal portion 56 and the proximal portion 54 have a similar pattern.

Figure 9A:
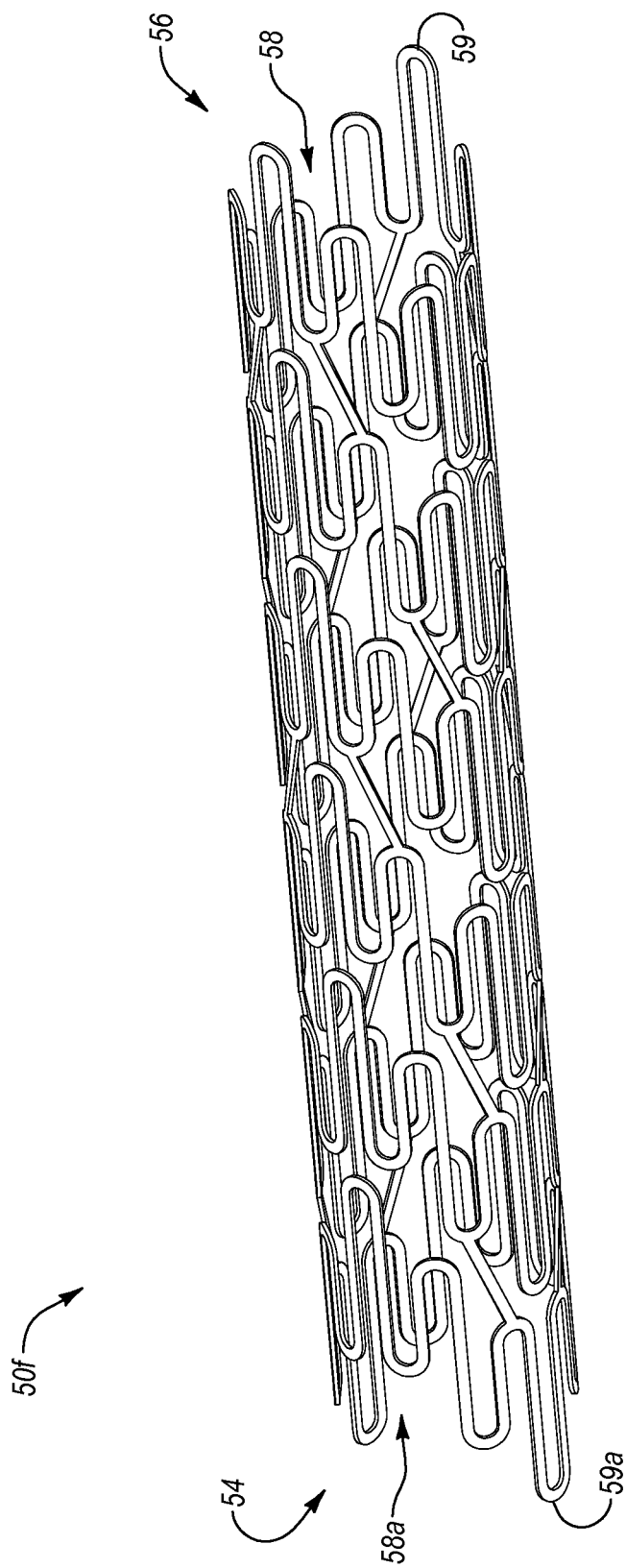
FIG. 9A is a perspective view of an endoprosthesis in an unexpanded configuration having cells rows arranged in a wave pattern that are connected by angled arm bars according to an implementation of the present invention.
Figure 9B:
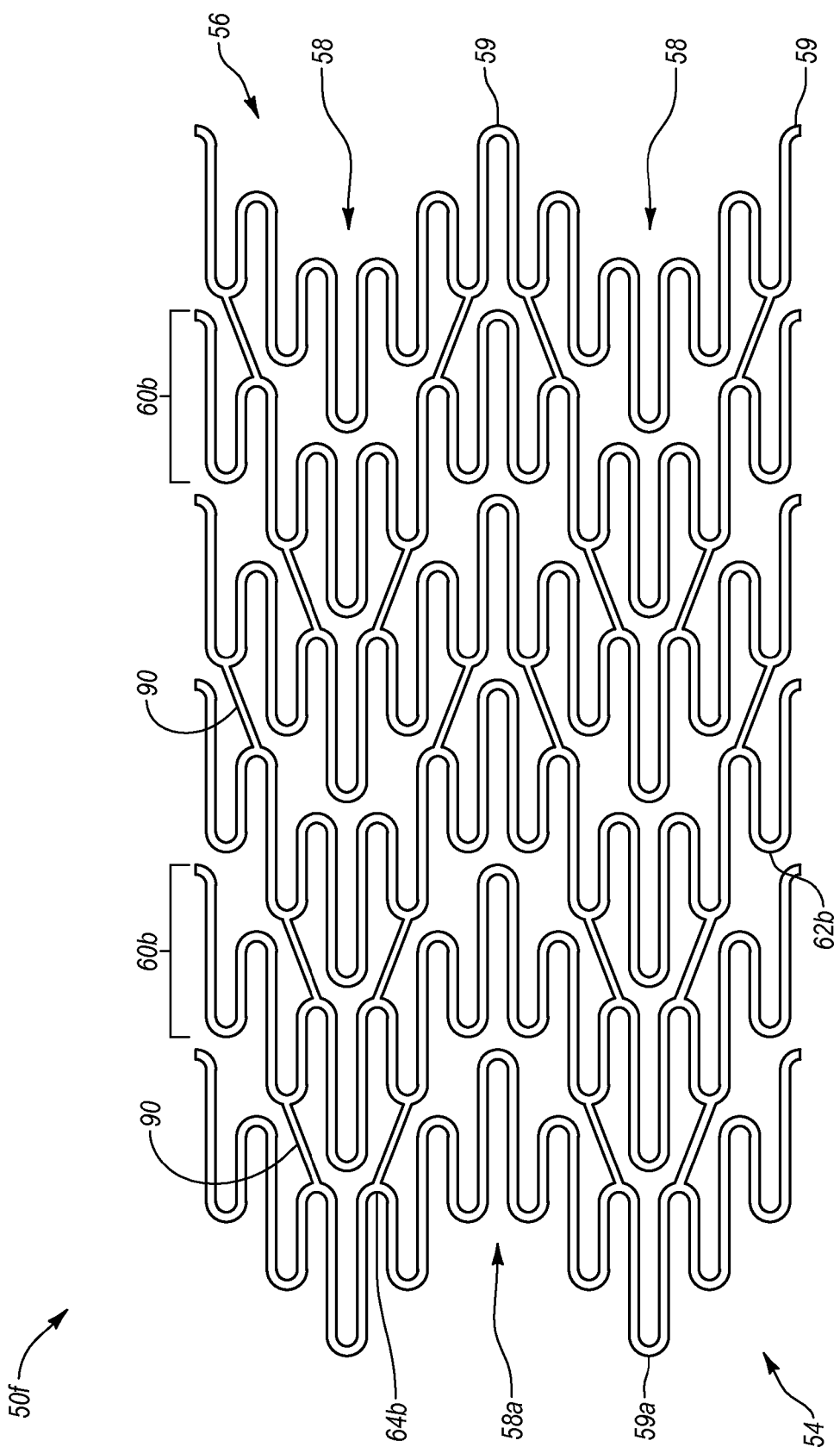
FIG. 9B is a flattened elevation view of the endoprosthesis of FIG. 9A.

As shown in FIGS. 9A-9B, the proximal portion 54 can include two or more wings 59a and two or more troughs 58a. Additionally, both the rings forming the proximal portion 54 and the distal portion 56 of the endoprosthesis 50f can be angled and secured together by angled inter-connectors 90. One will appreciate an endoprosthesis 50f with a uniform pattern can be used within a bifurcated lumen with a diameter that varies little or not at all along its length. Furthermore, an endoprosthesis 50f with a uniform pattern can increase manufacturing ease.

According to further implementations of the present invention, the endoprosthesis can have a configuration or pattern that varies along its length in order to allow the endoprosthesis to adequately scaffold a lumen that varies in diameter and shape along its length. For example, FIGS. 10A-10B, 11A-11B, and 12A-12B illustrate three endoprostheses 50g, 50h, and 50i that have configurations that vary along their length. The endoprostheses 50g, 50h, and 50i each have three portions or segments with differing configurations or patterns to provide differing expansion, strength, and flexibility characteristics to help the endoprostheses 50g, 50h, and 50i conform to the varying anatomy of a bifurcated lumen. In particular, the endoprostheses 50g, 50h, and 50i include a proximal region 54 with rings that have a pattern or configuration that provides uniform expansion and radial strength; a central or transition portion 55 with rings that have a pattern or configuration that provides radial strength with improved flexibility; and a distal portion 56 with rings that have a pattern or configuration that provides increased expansion and flexibility.

Figure 10A:
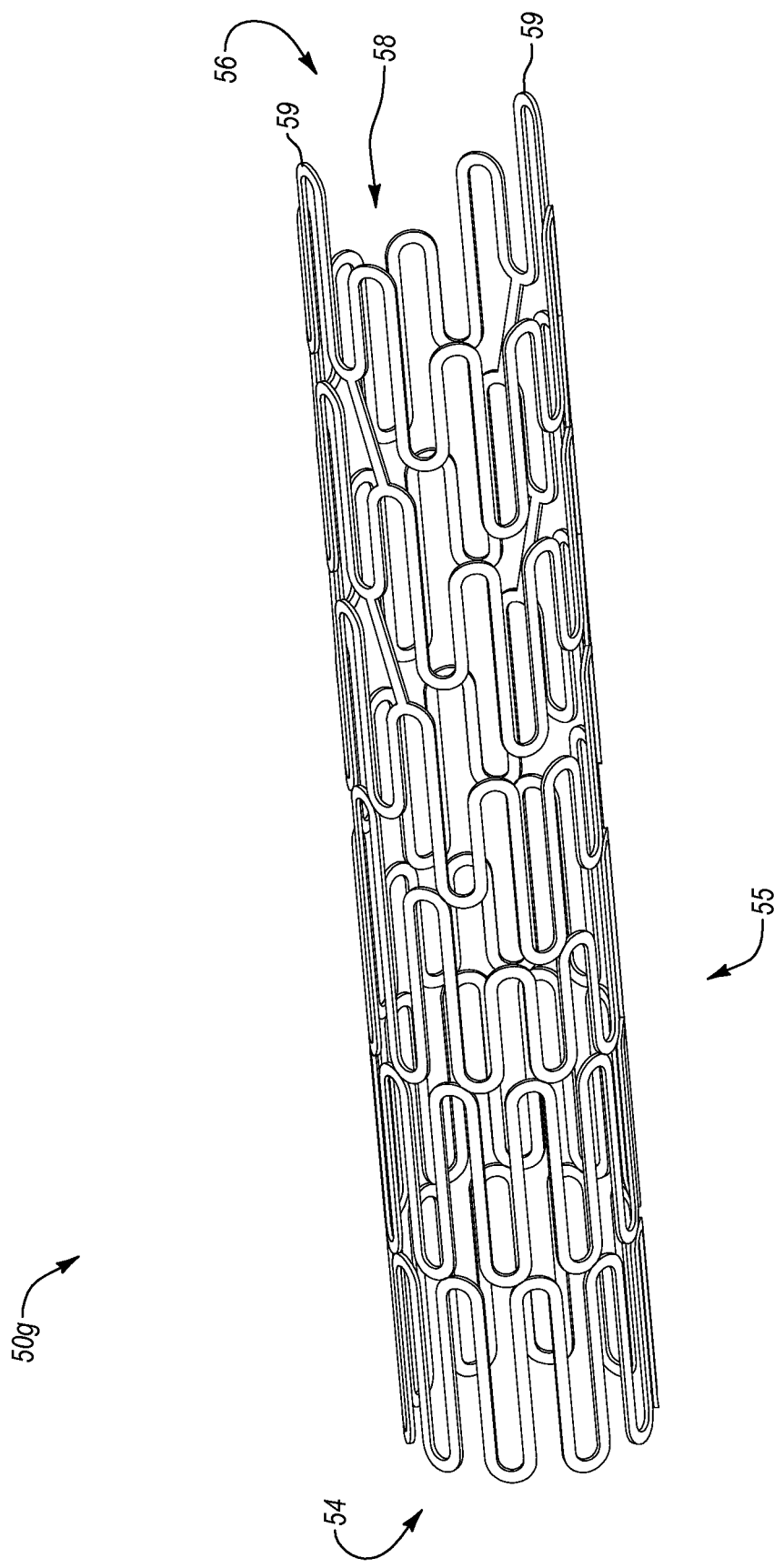
FIG. 10A is a perspective view of an endoprosthesis in an unexpanded configuration having several regions configured with different expandability according to an implementation of the present invention.
Figure 10B:
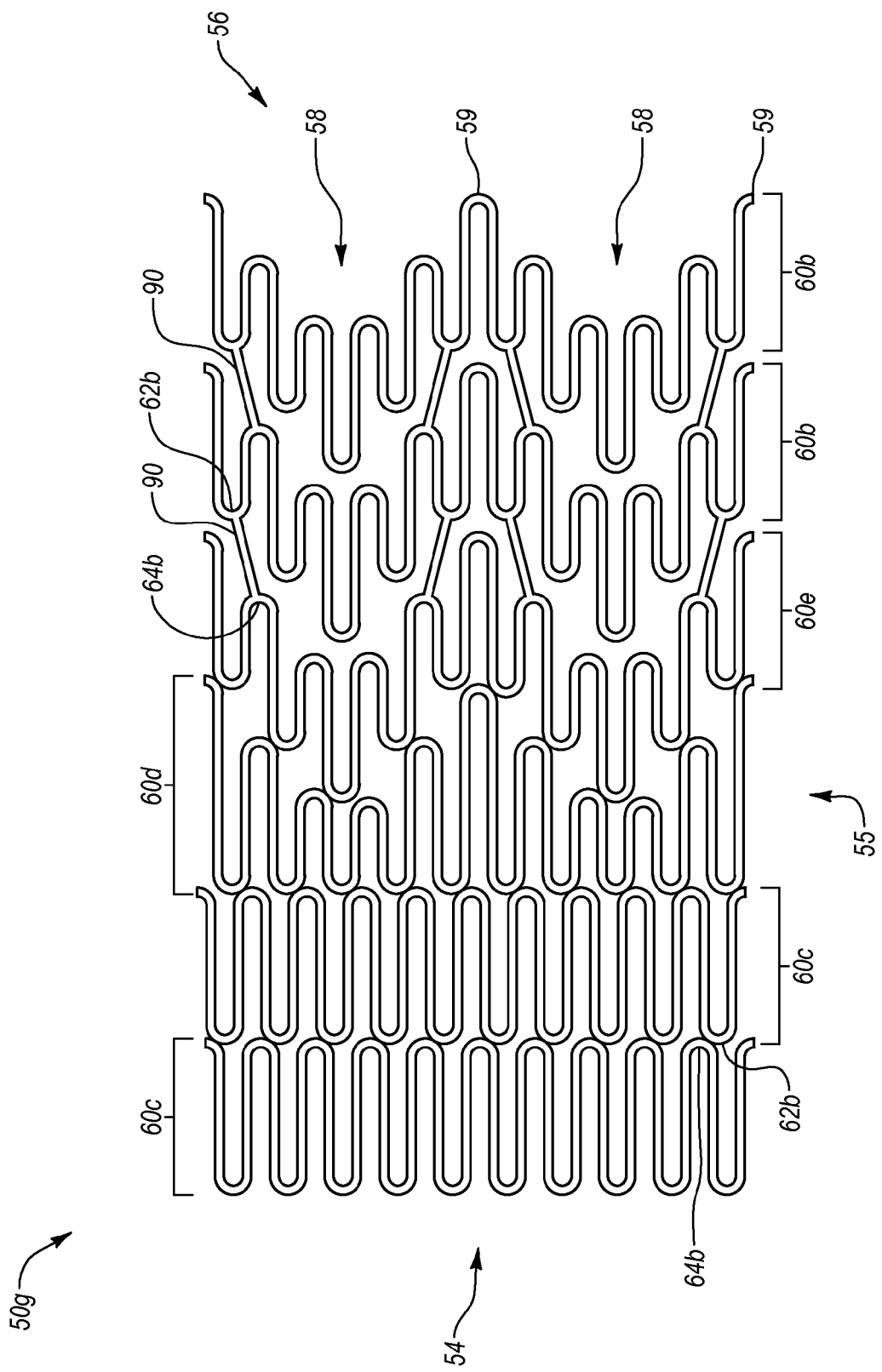
FIG. 10B is a flattened elevation view of the endoprosthesis of FIG. 10A.

Referring now to FIGS. 10A-10B, an endoprosthesis 50g is depicted that includes three regions with varying patterns or configurations to help allow the endoprosthesis 50g to conform to and adequately scaffold a bifurcated lumen. As shown in FIG. 10B, the apices of the valleys 62b and crests 64b of the rings 60c of the proximal portion 54 can each be directly interconnected. The direct interconnection of the rings 60c of the proximal portion 54 can increase the radial strength and scaffolding capabilities of the proximal portion 54 by reducing gaps between adjacent rings 60c. Additionally, each ring 60c of the proximal portion 54 can have the same shape and design to help provide for uniform expansion.

In contract to the proximal portion 54, the central or transition portion 55 can include rings 60d and 60e with differing shape and design. In particular, the rings 60d and 60e of the transition portion 55 provide a transition between the straight rings 60c of the proximal portion 54 and the angled rings 60b of the distal portion 56. The transitioning rings 60d, 60e can provide the central portion 55 with improved flexibility and expansion characteristics. Similar to the proximal portion 54, the apices of the valleys 62b and crests 64b of the rings 60d, 60e of the central portion 55 can each be directly interconnected to provide increased radial strength.

The rings 60b of the distal portion 56 of the endoprosthesis 50g can include some or all of the various features of the distal portions 56 of the endoprostheses described herein above to provide the distal end 56 with increased expandability and flexibility, allow the distal end 56 to adequately scaffold the ostium and side branches of bifurcated lumen, and prevent trauma to the carina of the bifurcated lumen. For example, the rings 60b of the distal end 56 can include wings 59 and troughs 58, can be angled, and can be indirectly connected to each other and the rings of the central portion 55 by angled inter-connectors 90.

Figure 11A:
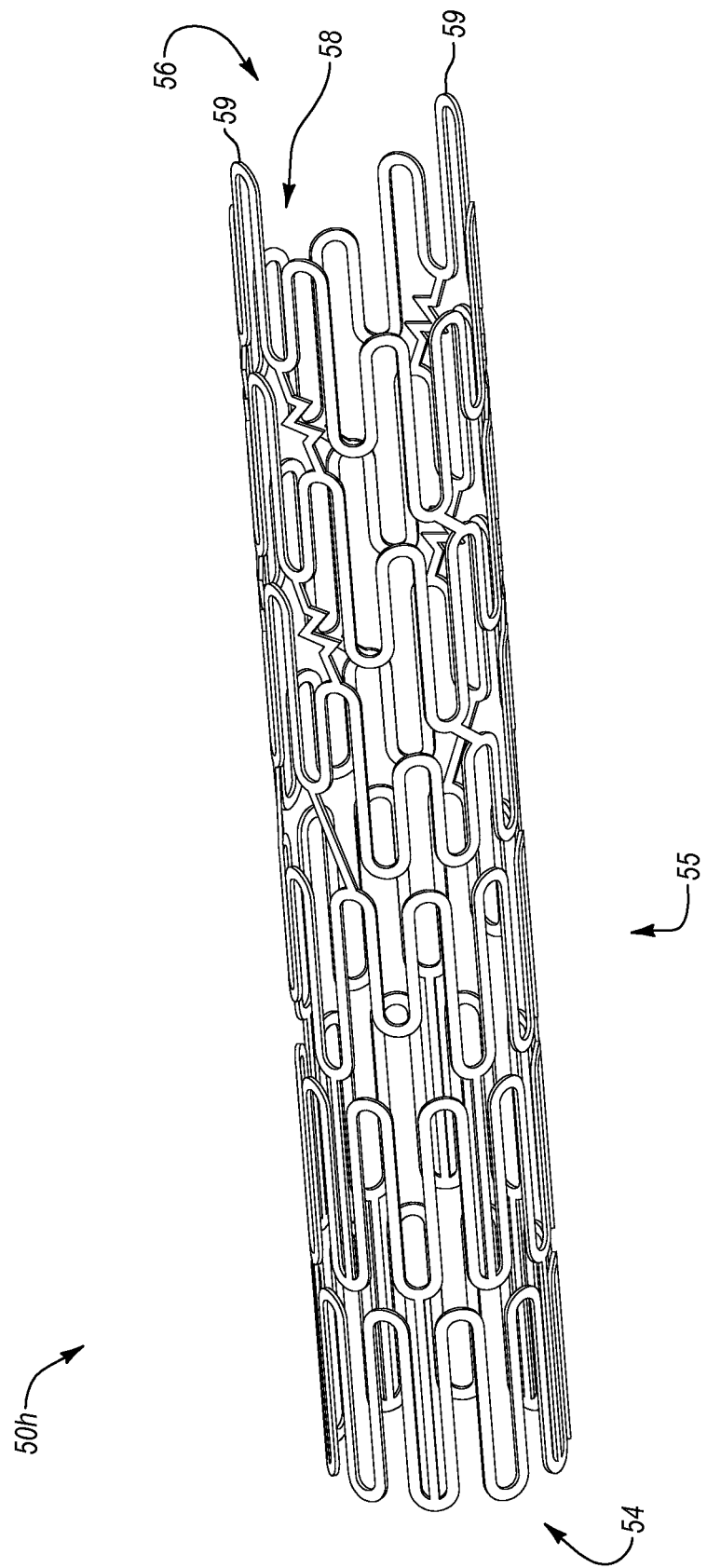
FIG. 11A is a perspective view of an endoprosthesis in an unexpanded configuration having several regions with different expandability interconnected by arm bars according to an implementation of the present invention.
Figure 11B:
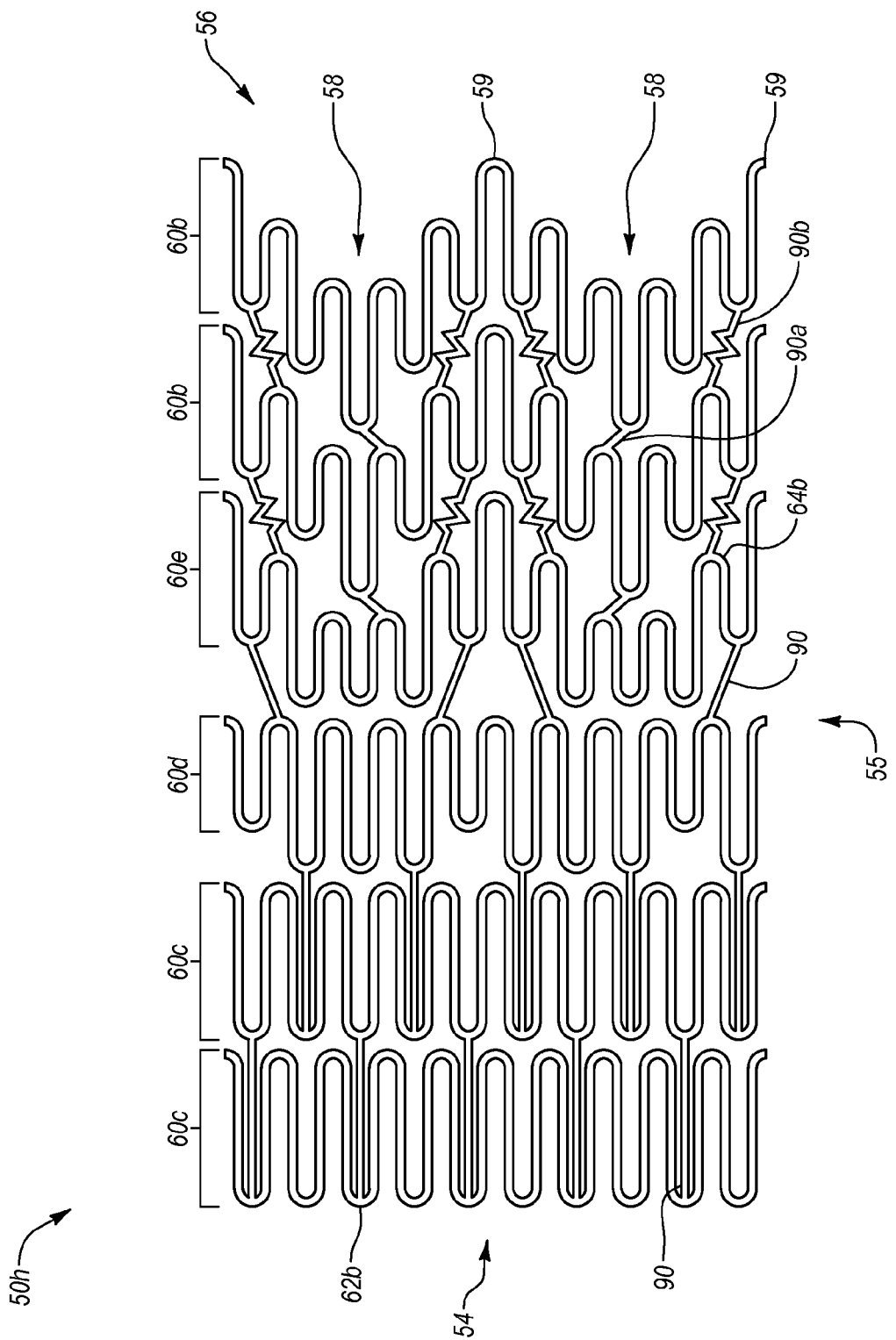
FIG. 11B is a flattened elevation view of the endoprosthesis of FIG. 11B.

In addition to varying the pattern of the rings, the type and placement of the inter-connections between rings can be varied to provide portions of the endoprosthesis with differing expansion, strength, and flexibility characteristics. For example, FIGS. 11A-11B illustrate an endoprosthesis 50h wherein the rings of the proximal portion 54, central portion 55, and distal portion 56 are all connected using inter-connectors of various type and placement to provide the portions 54, 55, 56 with varying expansion, strength, and flexibility characteristics. In particular, the rings 60c of the proximal portion 54 are connected by straight inter-connectors 90 that are positioned at least partially within one of the valley 62b and attach to an apex of a valley 64b of an adjacent row 60c.

In contrast, the rings 60d, 60e of the central portion 55 are connected by angled inter-connectors 90 extending between the apices of the crests 64b of one row 60d with the apices of the valleys 62b of an adjacent row 60e. One will appreciate that the angled inter-connectors 90 can provide the central portion 55 with increased flexibility and radial expandability.

Also, as shown in FIGS. 11A-11B, the rings 60b of the distal portion 56 can include shorter inter-connectors 90a to connect the crests 64b and valleys 62b forming the troughs 58 to help prevent the endoprosthesis from contacting the carina as much as possible. Additionally, the crests 64b and valleys 62b forming the wings 59 can be connected by expandable inter-connectors 90b that provide the distal end 56 of the endoprosthesis, and particularly the wings 59, with increased longitudinal expandability.

Figure 12A:
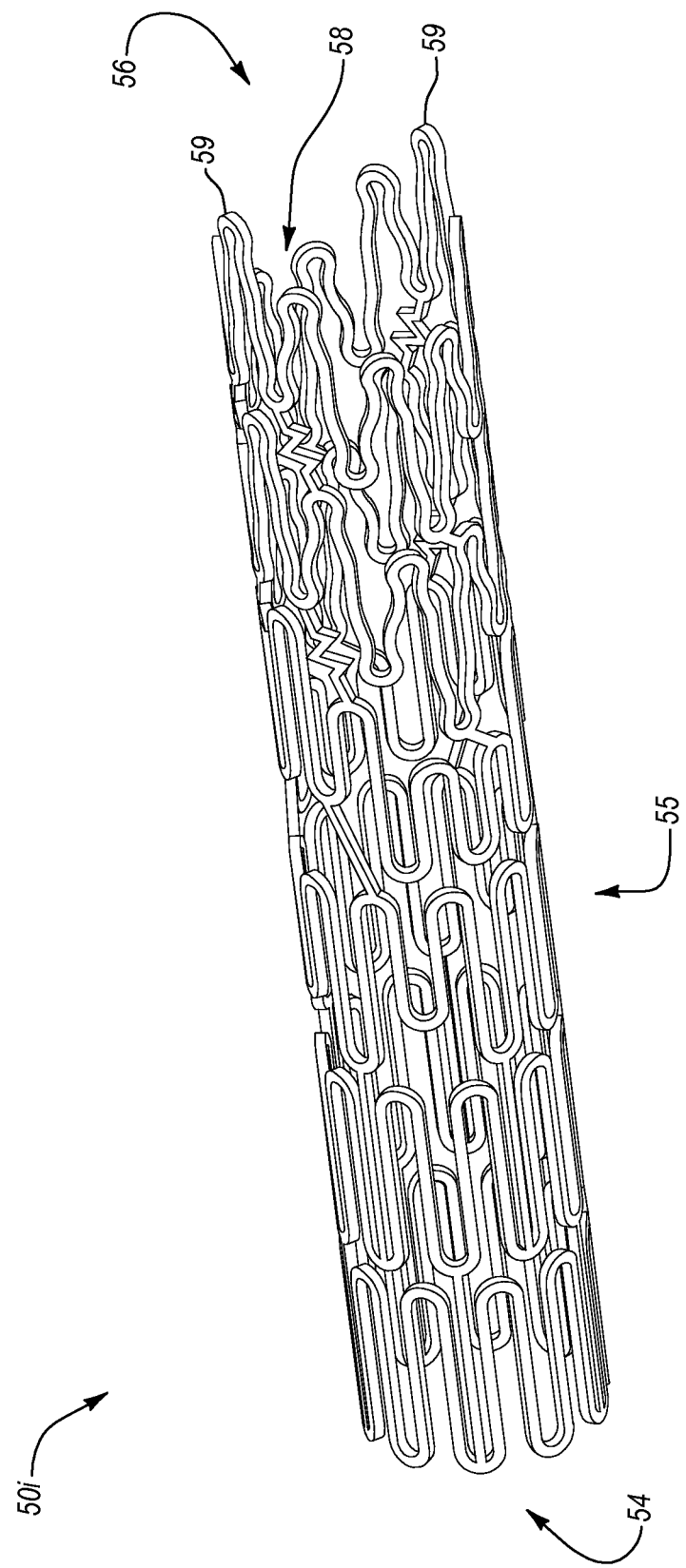
FIG. 12A is a perspective view of another endoprosthesis in an unexpanded configuration having several regions with different expandability according to another implementation of the present invention.
Figure 12B:
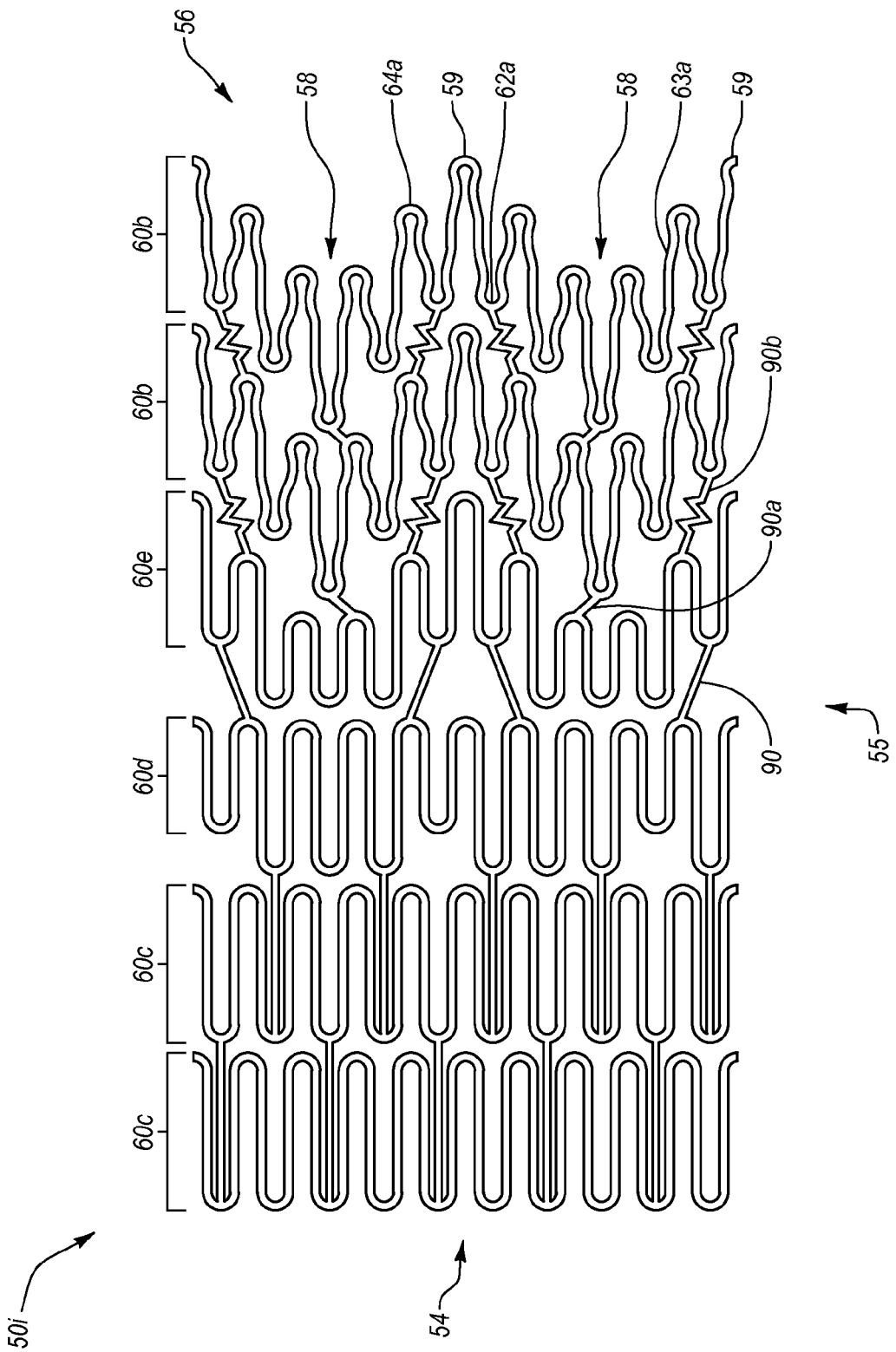
FIG. 12B is a flattened elevation view of the endoprosthesis of FIG. 12B.

Referring now to FIGS. 12A-12B, in addition to shorter inter-connectors 90a and expandable inter-connectors 90b, the rings 60f of the distal portion 56 can have a shape which provides increased expandability. For example, the rings 60f of the distal portion 56 can be configured to have a shape similar to that described herein above in relation to the endoprosthesis 50a depicted in FIG. 4A-4B. In particular, the crests 64a and the valleys 62a forming the rings 60f of the distal end 56 of the endoprosthesis 50i can be contoured. In particular, both the apices of the crest 64a and the valleys 62a can be curved to form a knob like structure. In other words, each apex of each ring 60a of the distal end 56 of the endoprosthesis 50f can have a semi-circular shape. Furthermore, the strut elements 63a connecting adjacent crests 64a and valleys 62a can also be curved such that the distance between adjacent strut elements 63a connected to a crest 64a or valley 62a decreases near the apex and then increases. One will appreciate that the curvature of the rings 60f can provide the distal end 56 with increased expandability as described herein above.

While the endoprostheses 50g, 50h, and 50i depicted and described in relation to FIGS. 10A-10B, 11A-11B, and 12A-12B each include three distinct portions or segments with differing configurations, one will appreciate that the present invention is not so limited. For example, the endoprostheses of the present invention can include as many differing regions or segments as need to allow them to conform to and adequately scaffold a bifurcated lumen, while helping ensure that the endoprosthesis does not injure the carina.

In addition to helping prevent trauma to the carina 22 (FIG. 1) of a lumen bifurcation, endoprostheses of the present invention can also help prevent trauma to the lumen walls within which they are deployed. For example, according to one implementation of the present invention, the outer surfaces of the endoprostheses of the present invention can include a coating. The coating can be biocompatible, or even biodegradable, and cover at least a portion of the outer surfaces of the endoprostheses that contact the inner surfaces of a lumen when deployed therein. The coating can be placed on top of the strut members forming the rings of the endoprosthesis body 52. Alternatively, the coating can cover the apertures between the cells (e.g., 40, 42 of FIG. 4B) of the endoprosthesis so as to form a sleeve over the endoprosthesis. One will appreciate that the coating can be configured to prevent adhesion of the tissue of the inner walls of the lumen to the endoprosthesis. Thus, the coating can help enable the endoprosthesis can be removed or repositioned without substantially tearing or damaging the repaired lumen.

Additionally, the endoprostheses of the present invention can include a distal portion formed from a first material and a proximal portion formed from a second material. For example, according to some implementations of the present invention the material forming the distal portion of the endoprosthesis can be selected to provide it with increased expandability and flexibility. While the material forming the proximal portion of the endoprosthesis can be selected to allow it to have uniform expandability and provide adequate support to a lumen. Alternatively, the proximal portion and the distal portion of the endoprosthesis can be formed from the same or similar materials. Generally, the materials for the endoprosthesis can be selected according to the structural performance and biological characteristics that are desired.

In one configuration, self-expanding embodiments of an endoprosthesis can include a material made from any of a variety of known suitable materials, such as a shaped memory material ("SMM"). For example, the SMM can be shaped in a manner that allows for restriction to induce a substantially tubular, linear orientation while within a lumen of a delivery device, but can automatically retain the memory shape of the endoprosthesis once extended from the delivery device. SMMs have a shape memory effect in which they can be made to remember a particular shape. Once a shape has been remembered, the SMM may be bent out of shape or deformed and then returned to its original shape by unloading from strain or heating. Typically, SMMs can be shape memory alloys ("SMA") comprised of metal alloys, or shape memory plastics ("SMP") comprised of polymers.

Usually, an SMA can have any non-characteristic initial shape that can then be configured into a memory shape by heating the SMA and conforming the SMA into the desired memory shape. After the SMA is cooled, the desired memory shape can be retained. This allows for the SMA to be bent, straightened, compacted, and placed into various contortions by the application of requisite forces; however, after the forces are released, the SMA can be capable of returning to the memory shape. Exemplary SMAs from which the endoprostheses of the present invention can be formed are as follows: copper-zinc-aluminium; copper-aluminium-nickel; nickel-titanium ("NiTi") alloys known as nitinol; and cobalt-chromium-nickel alloys or cobalt-chromium-nickel-molybdenum alloys known as elgiloy alloys. The temperatures at which the SMA changes its crystallographic structure are characteristic of the alloy, and can be tuned by varying the elemental ratios.

For example, the material of an endoprosthesis can be of a NiTi alloy that forms superelastic nitinol. In the present case, nitinol materials can be trained to remember a certain shape, straightened in a shaft, catheter, or other tube, and then released from the catheter or tube to return to its trained shape. Also, additional materials can be added to the nitinol depending on the desired characteristic.

An SMP is a shape-shifting plastic that can be fashioned into an endoprosthesis in accordance with the present invention. Also, it can be beneficial to include at least one layer of an SMA and at least one layer of an SMP to form a multilayered body; however, any appropriate combination of materials can be used to form a multilayered endoprosthesis. When an SMP encounters a temperature above the lowest melting point of the individual polymers, the blend makes a transition to a rubbery state. The elastic modulus can change more than two orders of magnitude across the transition temperature ("Ttr"). As such, an SMP can formed into a desired shape of an endoprosthesis by heating it above the Ttr, fixing the SMP into the new shape, and cooling the material below Ttr. The SMP can then be arranged into a temporary shape by force, and then resume the memory shape once the force has been applied. Exemplary SMPs from which the endoprostheses of the present invention can be formed include, but are not limited to, biodegradable polymers, such as oligo($\epsilon$-caprolactone)diol, oligo($\rho$-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

For example, VERIFLEX™, the trademark for CRG's family of shape memory polymer resin systems, currently functions on thermal activation which can be customizable from −20° F. to 520° F., allowing for customization within the normal body temperature. This allows an endoprosthesis having at least one layer comprised of VERIFLEX™ to be inserted into a delivery catheter. Once unrestrained by the delivery shaft, the body temperature can cause the endoprosthesis to return to its functional shape.

An endoprosthesis having at least one layer made of an SMM or suitable superelastic material and other suitable layers can be compressed or restrained in its delivery configuration within a delivery device using a sheath or similar restraint, and then deployed to its desired configuration at a deployment site by removal of the restraint as is known in the art. An endoprosthesis made of a thermally-sensitive material can be deployed by exposure of the endoprosthesis to a sufficient temperature to facilitate expansion as is known in the art.

Additionally, a self-expanding configuration of an endoprosthesis can include a biocompatible material capable of expansion upon exposure to the environment within the body lumen. Examples of such biocompatible materials can include a suitable hydrogel, hydrophilic polymer, biodegradable polymers, bioabsorbable polymers. Examples of such polymers can include poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly (beta-hydroxybutyrate), polyhydroxybutyrate-hydroxyvaleric acids, combinations thereof, or the like. For example, a self-expandable endoprosthesis can be delivered to the desired location in an isolated state, and then exposed to the aqueous environment of the body lumen to facilitate expansion.

Balloon-expandable endoprosthesis embodiments of the present invention can be comprised of a variety of known suitable deformable materials, including stainless steel, titanium, nickel-titanium (NiTi or nitinol), tantalum, cobalt-chromium, cobalt-chromium-vanadium, cobalt-chromium-tungsten, gold, silver, platinum, platinum-iridium or any combination of the foregoing metals and or alloys thereof. In addition to metals and metal alloys, balloon-expandable endoprosthesis of the present invention can be formed from other known biocompatible materials.

For example, balloon endoprosthesis embodiments of the present invention can include a suitable biocompatible polymer in addition to or in place of a suitable metal. The polymeric endoprosthesis can include biodegradable or bioabsorbable materials, which can be either plastically deformable or capable of being set in the deployed configuration. If plastically deformable, the material can be selected to allow the endoprosthesis to be expanded in a similar manner using an expandable member so as to have sufficient radial strength and scaffolding and also to minimize recoil once expanded. If the polymer is to be set in the deployed configuration, the expandable member can be provided with a heat source or infusion ports to provide the required catalyst to set or cure the polymer. Alternative known delivery devices and techniques for self-expanding endoprostheses likewise can be used.

Furthermore, the endoprostheses of the present invention can be formed from a ceramic material. In one aspect, the ceramic can be a biocompatible ceramic which optionally can be porous. Examples of suitable ceramic materials include hydroxylapatite, mullite, crystalline oxides, non-crystalline oxides, carbides, nitrides, silicides, borides, phosphides, sulfides, tellurides, selenides, aluminum oxide, silicon oxide, titanium oxide, zirconium oxide, alumina-zirconia, silicon carbide, titanium carbide, titanium boride, aluminum nitride, silicon nitride, ferrites, iron sulfide, and the like. Optionally, the ceramic can be provided as sinterable particles that are sintered into the shape of an endoprosthesis or layer thereof.

Moreover as mentioned above, the endoprostheses of the present invention can include a radiopaque material to increase visibility during placement. Optionally, the radiopaque material can be a layer or coating any portion of the endoprosthesis. The radiopaque materials can be platinum, tungsten, silver, stainless steel, gold, tantalum, bismuth, barium sulfate, or a similar material. Furthermore, any of the listed metals and metal alloys can be coated with a polymer containing fluorine-19, which is visible under MRI. Alternatively, other materials that are visible under MRI can be used in combination with the endoprostheses of the present invention. The radiopaque material can be applied as layers on selected surfaces of the endoprosthesis using any of a variety of well-known techniques, including cladding, bonding, adhesion, fusion, deposition or the like.

It is further contemplated that the external surface and/or internal surface of the endoprosthesis (e.g., exterior and luminal surfaces) can be coated with another material having a composition different from the primary endoprosthetic material. The use of a different material to coat the surfaces can be beneficial for imparting additional properties to the endoprosthesis, such as providing radiopaque characteristics, drug-reservoirs, and improved biocompatibility.

In one configuration, the external and/or internal surfaces of an endoprosthesis can be coated with a biocompatible material. Such coatings can include hydrogels, hydrophilic and/or hydrophobic compounds, and polypeptides, proteins or amino acids or the like. Specific examples can include polyethylene glycols, polyvinylpyrrolidone ("PVP"), polyvinylalcohol ("PVA"), parylene, heparin, phosphorylcholine, or the like.

The coatings can also be provided on the endoprosthesis to facilitate the loading or delivery of beneficial agents or drugs, such as therapeutic agents, pharmaceuticals and radiation therapies. As such, the endoprosthetic material and/or holes can be filled and/or coated with a biodegradable material.

Accordingly, the biodegradable material can contain a drug or beneficial agent to improve the use of the endoprosthesis. Such drugs or beneficial agents can include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors, as well as antineoplastics, antimitotics, antifibrins, antioxidants, agents that promote endothelial cell recovery, antiallergic substances, radiopaque agents, viral vectors having beneficial genes, genes, siRNA, antisense compounds, oligionucleotides, cell permeation enhancers, and combinations thereof.

Furthermore, it should be understood that any reference or claims to a drug or therapeutic agent being coated on the endoprosthesis can include one or more layers that are coated either directly on the endoprosthesis or onto a primer material. In particular, a primer material can be used on the endoprosthesis to which the drug or therapeutic agent readily attaches. This can be helpful when the endoprosthesis is formed from a metal because some drugs and therapeutic agents do not readily adhere to a metallic surface. Additionally, the drug or therapeutic agent can be combined with a coating or other medium used for controlled release rates of the drug or therapeutic agent.

In one configuration, the external surfaces of an endoprosthesis can include a coating comprised of polytetrafluoroethylene ("PTFE"), expanded PTFE ("ePTFE"), Dacron, woven materials, cut filaments, porous membranes, harvested vessels and/or arteries, or others such materials to form a stent graft prosthesis. Similarly, a medical device, such as a valve, a flow regulator or monitor device, can be used with the endoprosthesis, such that the endoprosthesis functions as an anchor for the medical device within the body lumen.

The endoprostheses of the present invention can be formed in any number of ways. For example, the endoprostheses of the present invention can be formed from a hollow tube using techniques, such as laser cutting, EDM, milling, chemical etching, hydro-cutting, and the like. Also, the endoprostheses of the present invention can be prepared to include multiple layers or coatings deposited through a cladding process such as vapor deposition, electroplating, spraying, or similar processes. Also, various other processes can be used such as those described below and or others known to those skilled in the art in light of the teachings contained herein.

Optionally, the endoprostheses of the present invention can be fabricated from a sheet of suitable material, where the sheet is rolled or bent about a longitudinal axis into the desired tubular shape. Additionally, either before or after being rolled into a tube, the material can be shaped to include endoprosthetic elements by being shaped with techniques such as laser-cutting, milling, etching or the like. If desired, the lateral edges of the structure can be joined together, such as by welding or bonding, to form a closed tubular structure, or the lateral edges can remain unattached to form a coiled, rolled sheet or open tubular structure. Such fabrication techniques are described in more detail below.

A method of making an endoprosthesis in accordance with the present invention can include sintering sinterable particles to provide a sintered article having the shape of the endoprosthesis. The sintering can be conducted in molds that are in the shape of an endoprosthesis.

In one configuration, the sintered body can be obtained from a molded green body prepared by molding a mixture of sinterable particles with or without a binder into the shape of an endoprosthesis or body intermediate. Sintering a molded green body that has the shape of an endoprosthesis can provide a sintered body that can function as an endoprosthesis with no or minimal further processing. Alternatively, after the green body has been formed in the mold and sintered into a hardened endoprosthesis, the process can include shaping the sintered body with a stream of energy and/or matter in order to obtain a desired shape. Thus, sintering a green body in a mold can result in an endoprosthesis that is either ready for use, or requires additional processing or finishing.

Additionally, the sintered body can be shaped into an endoprosthesis as described herein. Also, the endoprosthesis can be further processed after sintering and/or shaping such as by grinding, sanding, or the like to provide enhanced surface characteristics.

In another configuration, a multilayered endoprosthesis in accordance with the present invention can be prepared by a drawing process that draws two or more distinct concentric tubes into a single tube having two or more layers. Additionally, such a drawing process can combine multiple concentric tubes into a single multilayered tube. The drawing process can be configured to produce junctions separating adjacent layers or bonds that bond adjacent layers. As such, the sequentially-adjacent concentric tubes can be drawn together and progressively reduced in a cross-sectional profile until the desired size and residual clamping stress is attained.

Accordingly, a metallurgical bond can be prepared with elements of each sequentially-concentric tube diffusing together and bonding so as to form a strong metallurgical bond. Such a metallurgical bond can be achieved by applying significant pressure and heat to the tubes. As such, a metallurgical bond can form a diffusion layer at the interface between sequentially-adjacent concentric tubes (i.e., layers). The characteristics of these diffusion layers can be controlled by the proper heat treatment cycle. In part, this is because the heat treatment, temperature, and time of processing can control the rates of transfer of the diffusing elements that produce the diffusion layers. Also, the pressure at the interface between layers can be developed so as to result in the residual radial clamping stress in the tube after drawing.

In one example of this process, an outer tube of Nitinol, a middle tube of tantalum, and an inner tube of Nitinol can be arranged to form the composite structure. The multilayered material can be produced to result in bonding between the layers so as to achieve a residual clamping stress of at least about fifty p.s.i. Accordingly, the annealing process can be performed within a limited range of time and temperatures. For example, the lower limit can be at least about 1550° F. for at least six minutes, and the upper limit can be less than about 1850° F. for less than fifteen minutes.

In another configuration, a metallic interleaf layer can be placed between separate tubes so as to bond the tubes together and form a multilayered material. The multiple tubes separated by the metallic interleaf layer can be drawn together and progressively reduced until the desired cross-sectional profile and residual clamping stress is attained, as described above. The drawn tubes can be heat-treated to form a diffusion bond between the separate layers. As such, the metallic interleaf layer can enhance the diffusion rate or type of diffusing atoms that are transported across a diffusion region between one layer and the interleaf layer.

In one configuration, a multilayered sheet can be prepared to have separate layers of different materials or the same material. For example, the multilayered sheet can have a top layer of Nitinol, a middle layer of tantalum, and a bottom layer of Nitinol. The sheet can be prepared by metallurgically bonding the layers prior to a deep drawing process, which is well known in the art. During the deep drawing process, the sheet can be placed over a die and forced into the die, such as by a punch or the like. A tube having a closed end and a defined wall thickness can be formed in the die. This process can be repeated using a series of dies that have progressively decreasing diameters until a multilayered tube is formed having the desired diameter and wall thickness. For certain material combinations, intermediate heat treatments can be performed between the progressive drawing operations to form a multilayered material that is resistant to delaminating. Once a multilayered tube of desired thickness and dimensions has been formed, the closed end and the curved edges can be cut off. Then, the tube can be heat treated, as described above, until proper inter-metallic bonds are formed between the layers.

Accordingly, an endoprosthetic material can be shaped by various methods as described in more detail below. Such shaping techniques can utilize streams of energy and/or streams of matter in order to impart shapes into the endoprosthetic material. The streams of energy include photons, electromagnetic radiation, atomic, and sub-atomic materials, as described above. On the other hand, the streams of matter are considered to include materials larger than atomic scale particles, and can be microscopic or macroscopic in size. In any event, the shaping can be designed to direct a stream of energy or a stream of matter at the endoprosthetic material to form an endoprosthetic element and/or holes therein.

In one configuration, a stream of energy can cut, shape, and/or form a tube into an endoprostheses by generating heat at the site where the stream intersects the material, as is well known in the art. The thermal interaction can elevate the local temperature to a point, which can cut, melt, shape, and/or vaporize portions of the endoprosthetic material from the rest of the material.

Accordingly, one configuration of the stream-cutting apparatus can operate and shape the endoprosthetic material by thermal interactions. As such, any of the thermal processes described herein can be used for thermal-cutting. For example, such thermal interactions can arise from laser beam treatment, laser beam machining, electron beam machining, electrical discharge machining, ion beam machining, and plasma beam machining.

In one configuration, by knowing the thermal properties of the endoprosthetic material, precise energy requirements can be calculated so that the thermal beam provides the appropriate or minimum energy for melting and/or vaporizing the material without significantly melting undesirable portions of the material. For example, laser beams are a common form of a stream of energy that can be used to shape the endoprosthetic material. Additionally, there are instances where a laser is preferred over all other cutting techniques because of the nature of the resulting endoprosthesis as well as the characteristics of the endoprosthetic material.

In one configuration, an endoprosthesis may be manufactured as described herein using a femtosecond laser. A femtosecond laser may be desirable in producing an endoprosthesis in accordance with the multilayered composite structure of the present invention because it produces a smaller heat influence zone ("HIZ") or heat affected zone (HAZ) compared to other lasers, or it can substantially eliminate the HIZ or HAZ. In comparison, cutting an endoprosthesis using known methods can result in the tubular material being melted away, and thereby forming the pattern in the tubular member. Such melting can result in embrittlement of some materials due to oxygen uptake into the HIZ.

In one configuration, electrical discharge machining is used to shape endoprosthetic material and/or form holes in the endoprosthetic material as desired. As such, electrical discharge machining can be capable of cutting all types of conductive materials such as exotic metal including titanium, hastaloy, kovar, inconel, hard tool steels, carbides, and the like. In electrical discharge, the main interaction between the stream of energy and the endoprosthetic material is thermal, where heat is generated by producing electrical discharges. This can lead to the endoprosthetic material being removed by melting and evaporation. Some examples of electrical discharge machining include wire electron discharge machining, CNC-controlled electrical discharge machining, sinker electrical discharge machining, small hole discharge machining, and the like.

In another configuration, a charged particle beam can be used for shaping the endoprosthetic material, wherein electron beams and ion beams exemplify charged particle beams. A charged particle beam is a group of electrically-charged particles that have approximately the same kinetic energy and move in approximately the same direction. Usually, the kinetic energies are much higher than the thermal energies of similar particles at ordinary temperatures. The high kinetic energy and the directionality of these charged beams can be useful for cutting and shaping of the green bodies, as described herein. Additionally, there are some instances where electron beams or ion beams are preferred over other cutting techniques.

In one configuration, a stream of chemical matter can be used in order to shape or form holes in the endoprosthetic material. Chemical jet milling, for example, provides selective and controlled material removal by jet and chemical action. As such, the process is similar to water jet cutting, which is described in more detail below. In any event, chemical-jet milling can be useful for shaping various types of endoprosthetic materials, which provides intricate shaping capabilities.

In another configuration, electrochemical shaping can be based on a controlled electrochemical dissolution process similar to chemical jet milling an endoprosthetic material. As such, the endoprosthetic material can be attached to an electrical source in order to allow an electrical current to assist in the shaping.

In one configuration, hydro-cutting or water jet cutting can be used to shape an endoprosthetic material. Hydro-cutting is essentially a water jet technology that uses the high force and high pressure of a stream of water directed at the endoprosthetic material in order to cut and shape the material as desired. Hydro-cutting can be preferred over some of the other stream-cutting technologies because it can be free of heat, flame, and chemical reactions, and can provide a precise cold shaping technique. Also, heated water with or without being doped with reactive chemicals can also be used. Hydro-cutting is particularly suitable for polymeric endoprostheses, but can be used for metal materials when combined with abrasive particles, as described below.

Additionally, hydro-cutting can be enhanced by the introduction of particulate materials into the water feed line. As such, some hydro-cutting techniques utilize garnet or other rigid and strong materials in order to apply an abrasive cutting force along with the force applied by the water itself. Also, the hydro-cutting process in the present invention can be used with or without inclusion of such abrasives.

Additionally, one of the benefits of hydro-cutting is the ability to reutilize and recycle the spent water jet material. As such, the endoprosthetic material can be easily separated from the spent water, thereby enabling the recycling and reuse of the water during the hydro-cutting process.

In one configuration, sandblasting, which fits into the regime of stream of matter cutting, can be used to shape an endoprosthetic material by projecting a high energy stream of sand particles at the material. Sandblasting cuts materials in a manner similar to hydro-cutting, especially when the water jet is doped with abrasive particulates. Additionally, various other particulate streams other than sand can be used in the stream-cutting techniques and machinery.

An additional step of passivation can be performed during the manufacturing stage of the endoprosthesis in order to form a homogeneous oxide layer for corrosion-resistance. The passivation process may be performed prior to installation of the markers in accordance with the present invention or it may be performed after installation of the radiopaque markers. Alternatively, multiple passivation processes may be performed, once prior to application of the markers, and again after insertion of the markers.

As originally shaped and/or fabricated, the endoprosthesis can correspond to its delivery configuration, to a deployed configuration, or to a configuration therebetween. The endoprosthesis can be fabricated with a configuration at least slightly larger than the delivery configuration. In this manner, the endoprosthesis can be crimped or otherwise compressed into its delivery configuration in a corresponding delivery device.

The endoprostheses of the present invention can be designed to match the target lumen in which the endoprosthesis is to be deployed. For example, a stent can be provided with an outer diameter in the deployed configuration ranging from about 1 mm for neurological vessels to about 25 mm for the aorta. Similarly, a stent can be provided with a length ranging from about 5 mm to about 200 mm. Variations of these dimensions will be understood in the art based upon the intended application or indication for the endoprosthesis. Furthermore, as described herein above various regions of the endoprostheses of the present invention can be designed to expand to different diameters to match the anatomy of a bifurcated lumen.

The present invention may be embodied in other specific forms without departing from its spirit or essential characteristics. For example, a number of embodiments have been depicted and described hereinabove; these described embodiments are to be considered in all respects only as illustrative, not restrictive. Thus, the present invention also includes endoprostheses formed with a combination of some, or all of the features of the described embodiments. The scope of the invention is, therefore, indicated by the appended claims rather than by the foregoing description. All changes that come within the meaning and range of equivalency of the claims are to be embraced within their scope.

We claim:

1. An expandable endoprosthesis, comprising:
a tubular body having a distal end and a proximal end, a central longitudinal axis extending through the tubular body, a first plane and a second plane both parallel to the central longitudinal axis, the first plane and the second plane being orthogonal to each other, the distal end including at least two distally extending wing portions and at least two proximally extending recesses, the at least two distally extending wing portions being substantially symmetrical relative to both the first plane and the second plane, the at least two proximally extending recesses being substantially symmetrical relative to both the first plane and the second plane, the at least two distally extending wing portions and at least two proximally extending recesses being formed from at least one concentric ring having a plurality of alternating crests and valleys aligned in a wave pattern, a continuous inner surface of each at least two proximally extending recesses including a circumferentially extending transition recess intermediate a distal end of an adjacent wing portion and a proximal end of the recess, wherein the at least two proximally extending recesses extend the length of at least two concentric rings of the tubular body such that when deployed proximate a bifurcated lumen the at least two proximally extending recesses are configured to straddle a carina portion of the bifurcated lumen without substantially contacting the carina, and wherein expandability and flexibility of the expandable endoprosthesis increases from the proximal end to the distal end such that, when deployed proximate a bifurcated lumen, the distal end of the endoprosthesis may be expanded to a greater diameter than the proximal end and the at least two wing portions may extend into and along the lateral walls of the side branches of the bifurcated lumen.

2. The endoprosthesis as recited in claim 1, wherein the proximal end of the body is configured to expand from a contracted diameter to a first expanded diameter and at least a portion of the distal end of the body being configured to expand from the contracted diameter to a second expanded diameter that is larger than the first expanded diameter.

3. The endoprosthesis as recited in claim 1, wherein apices of the crests and valleys of the at least one concentric ring of the distal end have a semi-circular shape and are connected together by curved strut members.

4. The endoprosthesis as recited in claim 1, wherein the at least one concentric ring of the distal end comprises ten crests.

5. The endoprosthesis as recited in claim 1, wherein the at least one concentric ring of the distal end is secured to an adjacent concentric ring by a plurality of angled inter-connectors that extends between offset apices of valley and an adjacent crest.

6. An expandable endoprosthesis, comprising:
a tubular body having a distal end and a proximal end;
the proximal end of the body being configured to expand from a contracted diameter to a first expanded diameter; and
at least a portion of the distal end of the body being configured to expand from the contracted diameter to a second expanded diameter that is larger than the first expanded diameter;
wherein the distal end includes at least two distally extending wing portions formed from a web structure having a plurality of alternating crests and valleys and at least two recessed portions extending proximately into the distal end of the body between the at least two distally extending wing portions such that the distal end includes alternating wing portions and recessed portions, a continuous inner surface of each at least two proximally extending recesses including a circumferentially extending transition recess intermediate a distal end of an adjacent wing portion and a proximal end of the recess, and
wherein the distal end is configured in size and shape such that when deployed proximate a bifurcated lumen the at least two wing portions extend into and along the lateral walls of the side branches of the bifurcated lumen substantially without contacting a central wall portion of the bifurcated lumen;
wherein the distal end comprises a plurality of concentric rings having a plurality of alternating crests and valleys, the plurality of concentric rings being aligned in a wave pattern, the wave pattern defined by arranging the crests in a pattern of increasing and decreasing distal extent, such that crests having an increased distal extension form peaks of the wave pattern and crests having a decreased distal extension form troughs of the wave pattern;
wherein an inter-connector extends from each trough, adjacent to a distal-most peak forming one of the at least two distally extending wing portions of the distal concentric ring, and connecting the distal concentric ring with a longitudinally adjacent concentric ring of the plurality of concentric rings.

7. The endoprosthesis as recited in claim 6, wherein the two or more recessed portions and the two or more wing portions are sized and shaped to allow the distal end of the tubular body to straddle a carina of a bifurcated lumen substantially without contacting the carina.

8. The endoprosthesis as recited in claim 6, wherein the alternating wing portions and recessed portions are defined at least in part by at least one concentric ring, the at least one concentric ring including a plurality of alternating crests and valleys.

9. The endoprosthesis as recited in claim 8, wherein the at least one concentric ring is aligned in a wave pattern such that the peaks of the wave pattern define the at least two wing portions and the troughs of the wave pattern define the at least two recessed portions.

10. The endoprosthesis as recited in claim 6, wherein the proximal end of the tubular body is formed from a web structure including a plurality of diamond-shaped cells and the distal end of the tubular body is formed from a web structure including a plurality of rounded cells, wherein a first rounded cell is defined by an apex of a crest having a distal semi-circular shape, an apex of a valley having a proximal semi-circular shape, a first curved strut extending from a first end of the apex of the crest to a first end of the apex of the valley, a second curved strut extending from a second end of the apex of the crest to a second end of the apex of the valley, the first and second curved struts being convex relative to the crest and the valley.

11. An expandable, intraluminal endoprosthesis, comprising:
a tubular body having a length, proximal and distal ends, and a lumen extending therebetween;
at least two wing portions extending distally from the distal end of the tubular body, the at least two wing portions including a web structure having plurality of alternating crests and valleys; and
at least two recessed portions extending proximately into the distal end of the tubular body, wherein the at least two recessed portions extend proximally at least one quarter of the length of the tubular body;
wherein the distal end is configured in size and shape such that when deployed proximate a bifurcated lumen the at least two recessed portions straddle the carina substantially without contacting the carina of the bifurcated lumen and the at least two wing portions extend into and along the lateral walls of the side branches of the bifurcated lumen substantially without contacting a central wall portion of the bifurcated lumen;

wherein the distal end of the tubular body is formed from a web structure including a plurality of rounded cells, wherein a first rounded cell is defined by an apex of a crest having a distal semi-circular shape, an apex of a valley having a proximal semi-circular shape, a first curved strut extending from a first end of the apex of the crest to a first end of the apex of the valley, a second curved strut extending from a second end of the apex of the crest to a second end of the apex of the valley, the first and second curved struts being convex relative to the crest and the valley, the plurality of first and second curved struts forming a plurality of recesses along an inner surface of the at least two recessed portions.

12. The endoprosthesis as recited in claim 11, wherein the tubular body comprises a web pattern that includes a first web pattern and at least a second web pattern, wherein the web pattern changes from the first web pattern to the at least second web pattern along the length of the tubular body to correspond with the anatomy of a bifurcated lumen.

13. The endoprosthesis as recited in claim 12, wherein the tubular body comprises:
   a proximal portion with a web pattern configured to uniformly expand from a contracted diameter to a first expanded diameter; and
   a distal portion with a web pattern configured to expand from the contracted diameter to a second expanded diameter larger than the first expanded diameter.

14. The endoprosthesis as recited in claim 13, wherein the distal portion comprises a plurality of concentric rings having a plurality of alternating crests and valleys, the plurality of concentric rings being aligned in a wave pattern, the wave pattern defined by arranging the crests in a pattern of increasing and decreasing distal extent, such that crests having an increased distal extension form peaks of the wave pattern and crests having a decreased distal extension form troughs of the wave pattern.

15. The endoprosthesis as recited in claim 13, further comprising a central portion with a web pattern differing from the web patterns of the proximal portion and the distal portion.

16. An expandable endoprosthesis for treating a bifurcated lumen, comprising:
   a first set of concentric rings including a plurality of alternating crests and valleys defining a proximal end of a tubular body, wherein at least one crest or valley of each concentric ring of the first set of concentric rings is directly joined to a crest or valley of an adjacent concentric ring of the first set of concentric rings;
   a second set of concentric rings including a plurality of alternating crests and valleys defining a distal end of the tubular body, wherein at least one crest or valley of each concentric ring of the second set of concentric rings is indirectly joined to a crest or valley of an adjacent concentric ring of the second set of concentric rings by a plurality of angled inter-connecter elements, wherein at least two of the plurality of angled inter-connectors are non-parallel to each other such that the at least two of the plurality of angled inter-connectors extend away from each other or extend toward each other, two of the plurality of angled inter-connector elements extending from each valley adjacent a distal-most crest of a distal-most concentric ring of the second set of concentric rings; and
   wherein the distal end of the tubular body includes at least two distally extending wing portions formed by the plurality of alternating crests and valleys of the second set of concentric rings and at least two recessed portions extending proximally the length of at least two concentric rings of the tubular body, a continuous inner surface of each at least two proximally extending recesses including a circumferentially extending transition recess intermediate a distal end of an adjacent wing portion and a proximal end of the recess, and
   wherein the distal end is configured in size and shape such that when deployed proximate a bifurcated lumen the at least two recessed portions straddle the carina substantially without contacting the carina of the bifurcated lumen and the at least two wing portions extend into and along the lateral walls of the side branches of the bifurcated lumen substantially without contacting a central wall portion of the bifurcated lumen, and
   wherein the first set of concentric rings provides a first expandability and flexibility and the second set of concentric rings providing a second expandability such that the expandability and flexibility of the expandable endoprosthesis increases from the proximal end to the distal end.

17. The endoprosthesis as recited in claim 16, wherein the distal end includes alternating wing portions and recessed portions.

18. The endoprosthesis as recited in claim 16, wherein the one or more inter-connector elements is angled and secures an apex of a crest of one concentric ring to an apex of a valley of an adjacent concentric ring.

19. The endoprosthesis as recited in claim 16, wherein the distal most concentric ring of the second set of concentric rings includes ten crests.

20. The endoprosthesis as recited in claim 16, wherein the second set of concentric rings are aligned in a wave pattern such that the peaks of the wave pattern at least partially define the at least two wing portions and the troughs of the wave pattern define at least two recessed portions extending proximately into the distal end of the tubular body.

21. The endoprosthesis as recited in claim 3, wherein a first closed cell is defined by an apex of a crest having a distal semi-circular shape, an apex of a valley having a proximal semi-circular shape, a first curved strut extending from a first end of the apex of the crest to a first end of the apex of the valley, a second curved strut extending from a second end of the apex of the crest to a second end of the apex of the valley, the first and second curved struts being convex relative to the crest and the valley.

22. The endoprosthesis as recited in claim 3, wherein one of the at least one concentric rings of the distal end forms a plurality of closed cells, and wherein the closed cells are walnut-shaped.

23. The endoprosthesis as recited in claim 22, wherein one of the at least one concentric rings of the proximal end forms a plurality of closed cells, and wherein the closed cells are not walnut-shaped.

24. The endoprosthesis as recited in claim 5, wherein at least two of the plurality of angled inter-connectors are non-parallel to each other.

25. The endoprosthesis as recited in claim 5, wherein at least two of the plurality of angled inter-connectors extend away from each other or extend toward each other.

26. The endoprosthesis as recited in claim 1, wherein a distal end of each wing portion has a generally convex configuration that extends to a concave portion of the inner surface.

27. The endoprosthesis as recited in claim 1, wherein the inner surface of the recess comprises a stepped configuration extending from the distal end to the proximal end.

* * * * *